US009700352B2

(12) United States Patent
Honda et al.

(10) Patent No.: US 9,700,352 B2
(45) Date of Patent: Jul. 11, 2017

(54) CALCULUS RETRIEVING/REMOVING DEVICE AND METHOD

(71) Applicant: TERUMO KABUSHIKI KAISHA, Shibuya-ku (JP)

(72) Inventors: Kei Honda, Hadano (JP); Takeshi Tsubouchi, Chigasaki (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 263 days.

(21) Appl. No.: 14/499,685

(22) Filed: Sep. 29, 2014

(65) Prior Publication Data

US 2016/0089185 A1     Mar. 31, 2016

(51) Int. Cl.
*A61B 17/22* (2006.01)
*A61B 17/50* (2006.01)
*A61B 17/30* (2006.01)

(52) U.S. Cl.
CPC ............. *A61B 17/50* (2013.01); *A61B 17/22* (2013.01); *A61B 17/22031* (2013.01); *A61B 2017/22079* (2013.01); *A61B 2017/306* (2013.01)

(58) Field of Classification Search
CPC .......... A61B 17/22031; A61B 10/0283; A61B 2017/22035; A61B 2017/22079; A61B 2017/00561
See application file for complete search history.

(56) References Cited

U.S. PATENT DOCUMENTS

2009/0270808 A1* 10/2009 Mas ....................... A61B 17/22
604/119

* cited by examiner

*Primary Examiner* — Todd J Scherbel
*Assistant Examiner* — Son Dang
(74) *Attorney, Agent, or Firm* — Buchanan Ingersoll & Rooney PC

(57) ABSTRACT

A device for retrieving calculus in a lumen of a living body includes an elongated member possessing an outer dimension configured to be positioned in the lumen of the living body, wherein the tubular body includes an inlet, an outlet and a retrieval space in the interior at a position between the inlet and the outlet. A foldable sealing member is positioned in the tubular body interior and is axially movable in distal and proximal directions, and a plunger is connected to the sealing member so that axial movement of the plunger axially moves the sealing member in the interior of the tubular body. The foldable sealing member is folded into a folded configuration when the plunger is axially moved in a distal direction toward the inlet and being spread out in a spread-out configuration when the plunger is axially moved in a proximal direction away from the inlet.

20 Claims, 13 Drawing Sheets

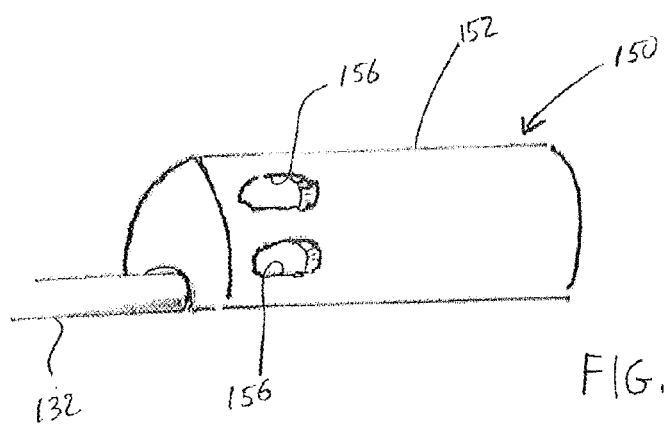
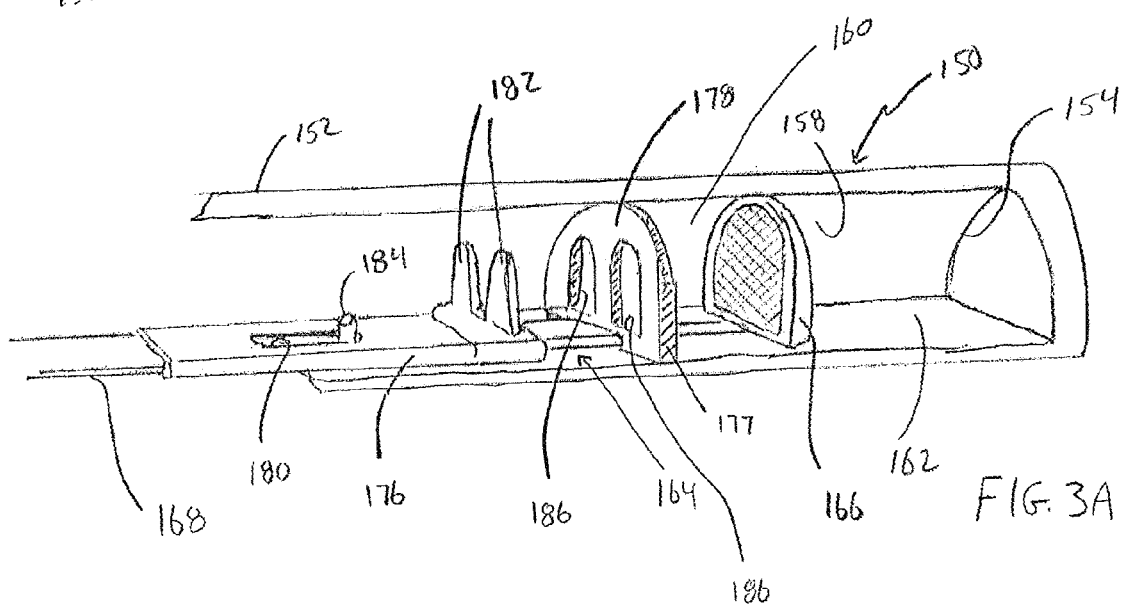

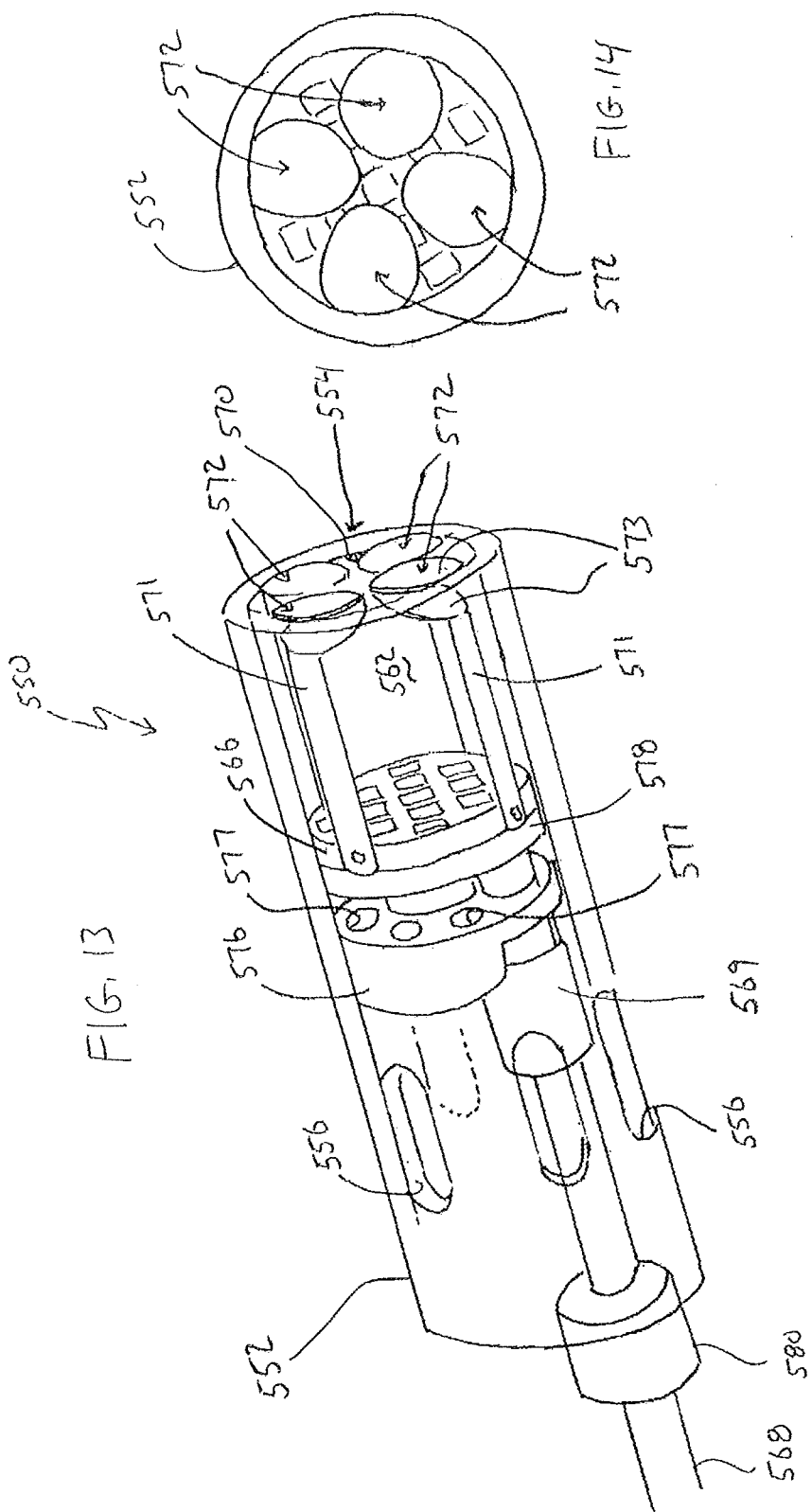

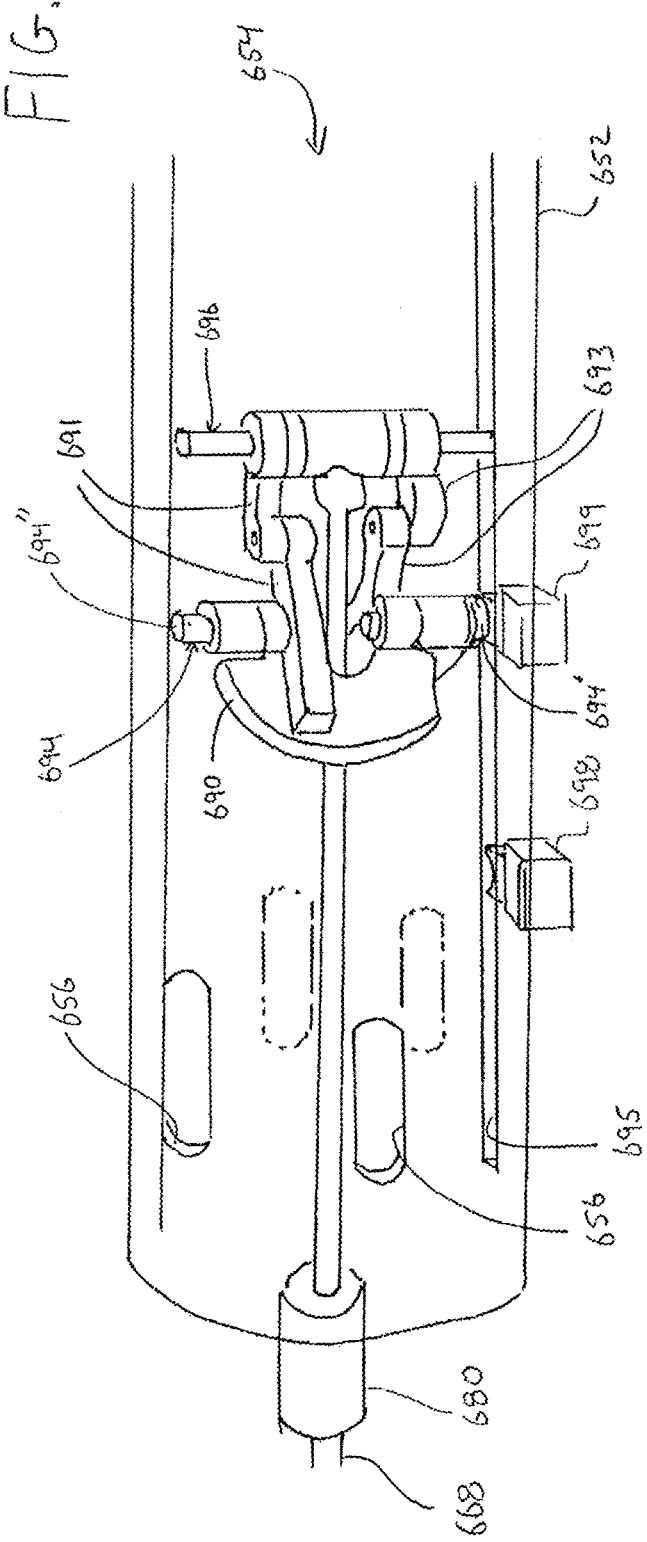

CALCULUS RETRIEVING/REMOVING DEVICE AND METHOD

CROSS-REFERENCE TO OTHER APPLICATIONS

This application discloses subject matter related to subject matter described in U.S. application Ser. No. 14/222,021, U.S. application Ser. No. 14/221,954 and U.S. application Ser. No. 14/221,858, the entire content of each of which is incorporated herein by reference.

TECHNICAL FIELD

The present invention generally pertains to methods and systems for retrieving/removing a mass from a human body. More specifically, the invention involves methods and systems for retrieving/removing stone(s) (e.g., calculus or calculi) from a portion of a human body such as the renal pelvis or the ureter.

BACKGROUND DISCUSSION

The term urinary calculus (e.g., kidney stones and ureteral stones) refers to masses or stones, typically solid particles, that form in the human body and are located in the kidneys and/or the ureter. They can exhibit a variety of chemical compositions including calcium oxalate, calcium phosphate, uric acid, cystine, and struvite.

Stone disease (e.g., kidney stones and ureteral stones) is a relatively common urological disorder. The presence of calculus in the body can manifest itself in a variety of ways and can produce a number of medical ailments. For example, the presence of calculus in the renal pelvis (kidney) can cause blood in the urine, urinary obstruction, infection, and various degrees of pain ranging from vague frank pain to much more severe pain not capable of being relieved through general pain medication. The presence of stones or calculi in the ureter can result in relatively severe side and back pain, pain below the ribs, and pain that sometimes spreads to the lower abdomen and groin, as well as pain during urination and hematuria.

Fortunately, many calculi or stones pass out of the body without requiring any specific medical intervention. In those situations where the calculus does not naturally pass out of the body, a medical procedure may be required. Known medical procedures typically fall into three categories.

In the past, three main treatments have been used to address calculus or kidney stones. These include shock wave lithotripsy (ESWL), transurethral lithotripsy or ureteroscopy (URS), and percutaneous nephroureterolithotripsy (PCNL) which is sometimes also referred to as percutaneous nephrolithotomy (PCN).

Shock wave lithotripsy is performed as an extracorporeal treatment. This treatment utilizes a machine called a lithotripter that operates by directing ultrasonic or shock waves from outside the body, through the skin and tissue, and at the calculi or stones. Repeated shock waves apply stress to the stones, eventually breaking the individual stones into smaller pieces which can more easily pass through the urinary tract in urine. One benefit associated with shock wave lithotripsy is that it is a rather simple procedure. But it has been found that there is a relatively high rate of kidney stone recurrence following shock wave lithotripsy.

Transurethral lithotripsy or ureteroscopy represents one such alternative form of treatment. This treatment involves the use of small fiber optic instrument called a ureteroscope which allows access to the calculus in the ureter or kidney. The ureteroscope can be a rigid ureteroscope or more commonly, a flexible ureteroscope. The ureteroscope allows the medical professional to visualize the stone as the ureteroscope moves along the ureter or enters the kidney by way of the bladder and the urethra. Once the calculus is visualized, a basket-like device is used to grasp smaller stones and remove them. If the calculus is excessively large to remove as a single piece, it can be broken into a smaller pieces by using laser energy.

The third form of treatment is percutaneous nephrolithotomy. This procedure is often used with relatively larger calculus that cannot be effectively treated with either ESWL or URS. Percutaneous nephrolithotomy involves nephrostomy; making an incision at the appropriate location, needling by paracentesis needle, positioning a guide wire through the paracentesis needle's lumen into the kidney under radiographic guidance, and then expanding perforated site. A nephroscope is then moved into the kidney via nephrostomy to visualize the calculus. Fragmentation of the calculus can be performed using an ultrasonic probe or laser.

Though these procedures have been commonly used, they are susceptible of certain short comings. For example, the ESWL procedure results in a relative large number of small calculi or small stones, while other procedures require a relatively narrow and long access route or are difficult to implement due to the inability to accurately capture the stones. In addition to, many crush pieces should be removed one by one in URS and PCNL procedure. The procedure time can also be excessively long, and can result in a relatively low "stone free rate." The recurrence rate can also be unacceptably high. And the potential patient complications (e.g., ischemia of the ureter, obstruction of ureter, back-flow and/or high-stress to the renal pelvis, infection of the urinary tract, and other possible injury) can be undesirably high.

SUMMARY

One aspect of the disclosure here involves a device for retrieving calculus in a lumen of a living body. The device includes an elongated member possessing an outer dimension configured to be positioned in the lumen of the living body, with the elongated member including a lumen and possessing an inner surface surrounding the lumen, and wherein the elongated member also includes an inlet, an outlet and a retrieval space in the lumen of the elongated member, with the outlet positioned proximally of the inlet and the retrieval space, and the retrieval space located proximally of the inlet. A foldable sealing member is movably positioned in the lumen of the elongated member to axially move in a distal direction in the lumen of the elongated member toward the inlet of the of the elongated member and to axially move in a proximal direction in the lumen of the elongated member. The foldable sealing member includes at least one part that possesses an outer surface and is foldable so that the sealing member is shiftable between: an unfolded spread position in which the part is unfolded and spread out with the outer surface of the one part of the sealing member in sealing contact with the inner surface surrounding the lumen of the elongated member when the plunger is axially moved in the proximal direction to draw the calculus and fluid in the lumen of the living body into the retrieval space; and a folded position in which the one part is folded when the plunger is axially moved in the distal direction to permit fluid in the retrieval space to pass the foldable sealing member.

In accordance with another aspect, a device for retrieving calculus in a lumen of a living body comprises: an elongated member possessing a distal end portion and an outer dimension configured to permit the elongated member to be positioned in the lumen of the living body, with the distal end portion of the elongated member being a tubular body possessing an interior surrounded by an inner surface; wherein the tubular body includes an inlet, an outlet and a retrieval space in the interior at a position between the inlet and the outlet; a foldable sealing member positioned in the interior of the tubular body and axially movable in a distal direction and in a proximal direction; and a plunger connected to the sealing member so that axial movement of the plunger axially moves the sealing member in the interior of the tubular body. The foldable sealing member is folded into a folded configuration when the plunger is axially moved in a distal direction toward the inlet and being spread out in a spread-out configuration when the plunger is axially moved in a proximal direction away from the inlet.

Other features and aspects of the calculus retrieving/removing device and method disclosed here will become more apparent from the following detailed description considered with reference to the accompanying drawing figures in which like elements are designated by like reference numerals.

BRIEF DESCRIPTION OF DRAWINGS

FIG. 2 is a perspective outside view of a calculus removing/retrieving device representing another example of the calculus removing/retrieving device disclosed here used to carry out an aspect of the disclosed method.

FIG. 3A is a perspective view similar to FIG. 2, but illustrating, in an enlarged manner, features associated with the calculus removing/retrieving device when the sealing member is in an open condition or state.

FIG. 13 is a perspective view of a calculus removing/retrieving device representing another example of the calculus removing/retrieving device disclosed here.

FIG. 14 is a front end view of the calculus removing/retrieving device shown in FIG. 13.

FIG. 16 is a perspective view of a calculus removing/retrieving device representing another example of the calculus removing/retrieving device disclosed here.

DETAILED DESCRIPTION

Set forth below is a detailed description of features and aspects of the calculus removing/retrieving device and method described here as examples of the disclosed invention. The methods and devices disclosed here for removing/retrieving calculus have particularly useful application to retrieve and remove calculus located in the ureter (ureter stones) and calculus located in the renal pelvis (kidney stones), though the methods and evokes are not limited in that regard.

Generally speaking, the calculus removing/retrieving device disclosed here, as represented by the several embodiments representing examples of the inventive calculus removing/retrieving device (and method), is configured to be positioned inside a living body at a position adjacent the location of calculus to be removed from the living body. The calculi (stones) are drawn into the interior of the device by causing a sealing member positioned within the interior of a body to axially move within the interior of the device. As the sealing member moves in the rearward direction within the interior of the body, calculus is drawn into the interior of the body. But during subsequent forward movement of the sealing member, the calculus remains in the interior of the body and is not ejected out through the inlet.

Figure 1:
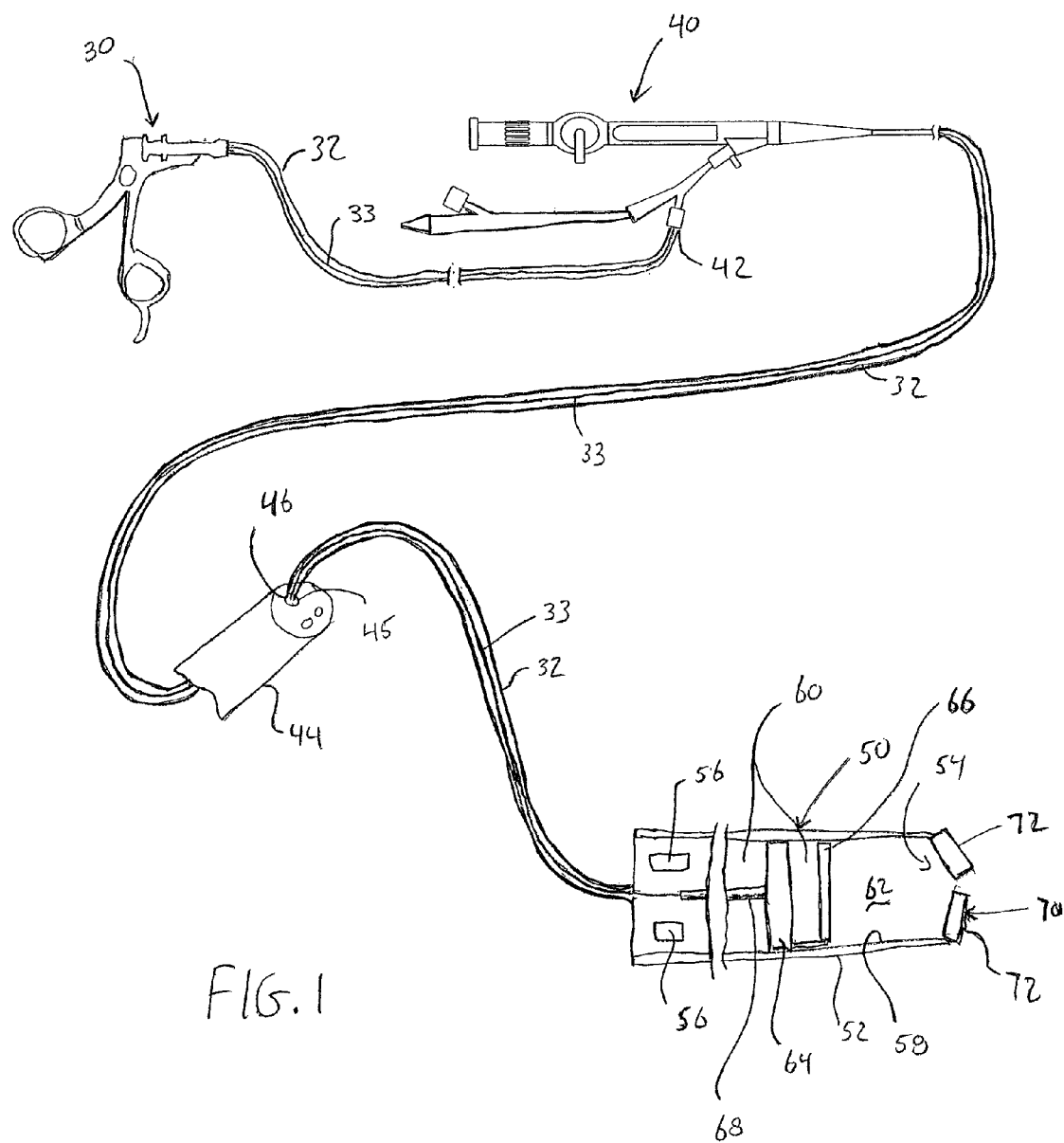
FIG. 1 is a schematic illustration of a calculus removing/retrieving device connected to an operation member through the intermediary of a ureteroscope

Turing now to the drawing figures, FIG. 1 illustrates, in a schematic manner, one version of the calculus removing/retrieving device 50. As illustrated in FIG. 1, the calculus removing/retrieving device 50 can be used together with an operating member 30 and an ureteroscope 40. The operating member 30 is connected to tubing 32 and a manipulation wire 33 possessing sufficient flexibility/rigidity characteristics to allow the operation described below. The manipulation wire 33 passes through the lumen which extends along the tubing 32. The tubing 32 and the manipulation wire extend from the operating member 30, enters an inlet 42 of an instrument channel 46 in the ureteroscope 40, passes through the ureteroscope 40 and exits at an outlet 45 at the distal end portion 44 of the ureteroscope, and is connected to the calculus removing/retrieving device 50. The distal end portion of the tubing 32 is connected to a proximal end surface of the calculus removing/retrieving device 50. A distal end portion of manipulation wire 33 is connected to an elongated plunger 68.

As generally illustrated in FIG. 1, the calculus removing/retrieving device 50 includes an elongated member 52. In this illustrated embodiment, the elongated member 52 is a tubular body possessing an inlet 54, an outlet(s) 56, and a lumen extending along the length of the tubular body 52 to define an interior 60 of the tubular body 52. The interior (lumen) 60 of the tubular body 452 is surrounded by the inner surface 58 of the tubular body 52. In this embodiment, the outlet 56 is in the form of plural outlets. Also, the outlet(s) is provided in the wall of the tubular body 52, whereas the inlet is provided at the axial end of the tubular body. Further, the outlet(s) 56 is positioned proximally of the inlet 54.

A sealing member 64 is positioned in the interior 60 of the tubular body 52 and is configured to axially move within the interior of the tubular body. The outer peripheral surface of the sealing member 64 contacts the inner surface 58 of the tubular body to provide a seal between the sealing member 64 and the inner surface 58 of the tubular body. That is, the sealing member 64 is substantially in sealing contact with the inner surface 58 of the tubular body 52. The phrase "substantially in sealing contact" with the inner surface of the tubular body means that the sealing member is in sealing contact with the inner surface, except for some leakage between the sealing member 64 and the tubular body 52 that does not materially alter the method/operational aspects of the device. A filter 66 is fixed to the sealing member 64. The sealing member 64 and the filter 66 are connected to each other so that the two move together in unison. The sealing member 64 can be in the form of a gasket.

The sealing member 64 is fixed to the elongated plunger 68. That is, the distal end of the plunger 68 is connected to the sealing member 64 so that axial movement of the plunger 68 results in axial movement of the sealing member. The plunger 68 also possesses a proximal end connected to the manipulation wire 33.

By virtue of the construction illustrated in FIG. 1, when the operating member 30 is operated by the operator/user (e.g., medical professional) to pull the manipulation wire 33 in the rearward or proximal direction, the plunger 68 and the filter 66 also move in the rearward or proximal direction within the interior of the tubular body 52 (i.e., to the left in FIG. 1). When the operating member 30 is operated by the operator/user to push the manipulation wire 33 in the forward or distal direction, the sealing member 64 and the filter 66 move together in the forward or distal direction (i.e., to the right in FIG. 1).

The calculus removing/retrieving device 50 further includes a barrier member 70 mounted adjacent the inlet of the tubular body. The barrier member 70 is comprised of several individual barriers or cover parts 72. The barriers 72 are preferably mounted on the distal end of the tubular body 52 in a manner allowing the barriers to pivot between an open position of the barriers 72 (open condition of the barrier member 70) which permits calculus and fluid to be drawn through the inlet 54 of the tubular body 52 and into a retrieval space 62 in the interior of the tubular body, and a closed position of the barriers 72 (closed condition of the barrier member 70) which prevents calculus located in the retrieval space 62 from being discharged out through the inlet 54 past the barrier member 70. The retrieval space 62 is located axially between the sealing member 64 and the barrier member 70, and the filter 66 is located axially between the retrieval space 62 and the sealing member 64.

Generally speaking, the operation of the calculus removing/retrieving device 50 and associated instrumentation shown in FIG. 1 is as follows. First, the plunger 68 of the calculus removing/retrieving device 50 is connected to the manipulation wire 33. The proximal end of the tubing 32 and the manipulation wire 33 are introduced into the instrument channel 46 by way of the outlet 45 at the distal end portion 44 of the ureteroscope 40. The tubing 32 and the manipulation wire 33 are moved along the instrument channel 46 and conveyed out of the channel inlet 42, and the proximal end of the tubing 32 and the manipulation wire 33 are then connected to the operating member 30. The calculus removing/retrieving device 50 can then be positioned in the living body and advanced to the desired location for removing calculi (stones) in the living body. As mentioned above, the tubing 32 and the manipulation wire 33 possess sufficient rigidity, yet are sufficiently flexible, to properly advance the calculus removing/retrieving device 50 along the necessary part of the living body to position the inlet 54 of the tubular body 52 adjacent the calculus to be retrieved and removed. For example, to retrieve and remove calculi or ureter stones in the ureter, the calculus removing/retrieving device can be introduced into the ureter by way of the urethra and the bladder. If the calculus removing/retrieving device is used to retrieve and remove calculi or kidney stones from the renal pelvis, the calculus removing/retrieving device can be inserted into the living body, for example by way of the urethra, passed through the bladder and moved along the ureter until entering the renal pelvis. The calculus removing/retrieving device 50 is then positioned to locate the inlet 54 of the tubular body 52 at a position close to or adjacent the calculus to be removed.

When the calculus removing/retrieving device 50 is positioned at the desired location, the operator/user operates the operating member 30 to pull (move) the manipulation wire 33 in the proximal or rearward direction. This thus moves the plunger 68 in the proximal or rearward direction (i.e., to the left in FIG. 1) which in turn causes the sealing member 64 as well as the filter 66 to move in the proximal or rearward direction. As the sealing member 64 moves in the proximal direction within the interior (lumen) of the tubular body, the sealing member 64 produces a suction force that draws or sucks stone(s) (calculus or calculi) and fluid through the inlet 54 and into the retrieval space 62 in the interior 60 of the tubular body 52. The filter 66 is specifically sized to permit the passage of fluid, yet prevent the passage of calculus that has been retrieved in the retrieval part 62. Thus, when the plunger 68 is pulled in the rearward or proximal direction, water and calculus are sucked into the retrieval space 62 by way of the inlet 54, and water is permitted to simultaneously exhaust through the outlet 56. The hingedly or pivotally mounted barriers 72 are able to pivot inwardly toward the retrieval space 62 as a result of the suction force created by the rearward movement of the sealing member 64 inside the tubular body 52. This inward pivoting of the barriers 72 opens the barrier member 70 (barriers 72) to allow calculus and fluid to enter the interior of the tubular body 52. The barriers 72 (barrier member 70) thus does not present an impediment to drawing calculus I to the retrieval space 62.

As will become more apparent from the description below, the sealing member 64 can be provided with, for example, through holes so that at least some of the fluid (water) being sucked into the retrieval space 62 by way of the inlet 54 is exhausted through the outlet 56 while the sealing member 64 is being axially moved in the proximal or rearward direction.

The operation of the operating member 30 causing the rearward axial movement of the sealing member 64 in the proximal direction is then stopped so that the axial movement of the sealing member 64 in the rearward or proximal direction ceases. Next, the operating member 30 is operated to move the manipulation wire 33 in the forward or distal direction to thus also move the plunger 68, the sealing member 64 and the filter 66 in the forward or distal direction (i.e., to the right in FIG. 1). The movement of the sealing member 64 in the forward or distal direction causes the barriers 72 to pivot in a direction away from the interior of the tubular body so that the barriers 72 (barrier member 70) shifts to the closed positioned generally illustrated in FIG. 1. As will be described in more detail below in connection with other embodiments of the calculus removing/retrieving device, the barriers 72 are configured so that in the closed position, fluid is permitted to flow from the interior 60 (retrieval space 62) of the tubular body 52 through the inlet 54 and to the outside of the calculus removing/retrieving device, yet calculus that has been sucked into, and is located in, the retrieval space 62 is prevented from flowing outwardly through the inlet 54 to the outside of the calculus removing/retrieving device. As the sealing member 64 moves in the forward or distal direction, fluid also passes through the filter 66 and the retrieval space 62, and out through the inlet 54, but the barriers 72 in the closed position prevent calculus in the retrieval space 62 from flowing out through the inlet 54. It is possible to repeat the movement of the sealing member 64 in the proximal direction and the moving of the sealing member 64 in the distal direction in a continuous manner to generate fluid flow from the inlet 54 to outlet 45 in the elongated member.

FIGS. 2, 3A and 3B 3 illustrate an embodiment of the calculus removing/retrieving device 150 representing another example of the calculus removing/retrieving device and operational method disclosed here. Features of this embodiment which are similar to features described in the earlier embodiment are identified by common reference numerals, but preceded by a "1". A detailed description of features in this embodiment that are similar to features in the earlier embodiment is not repeated, and the following detailed description focuses primarily on differences between this embodiment and the earlier embodiment.

FIG. 2 illustrates that the calculus removing/retrieving device 150 includes an elongated member or tubular body 152 having a generally rounded triangular exterior shape as seen in a cross section perpendicular to the central longitudinal axis of the tubular body 152. As illustrated in FIG. 3A, this embodiment of the calculus removing/retrieving device 150 includes a multi-part sealing member 164. That is, the sealing member 164 is comprised of a first part 176 and a second part 178. The distal end of the plunger 168 is fixed to the second part 178 of the sealing member 164, and the first part 176 of the sealing member 164 is slidably mounted on the plunger 168 so that the first and second parts 176, 178 of the sealing member 164 are relatively axially movable, over a limited axial distance or axial extent, relative to one another. The first part 176 of the sealing member 164 includes an elongated slot 180 extending along the longitudinal extent of the first part 176. The first part 176 of the sealing member 164 also includes several upstanding cover elements 182. The cover elements 182 are fixed to the first part 176 of the sealing member 164 so that the cover elements 182 and the first part 176 of the sealing member 164 move together as a unit.

Figure 3B:
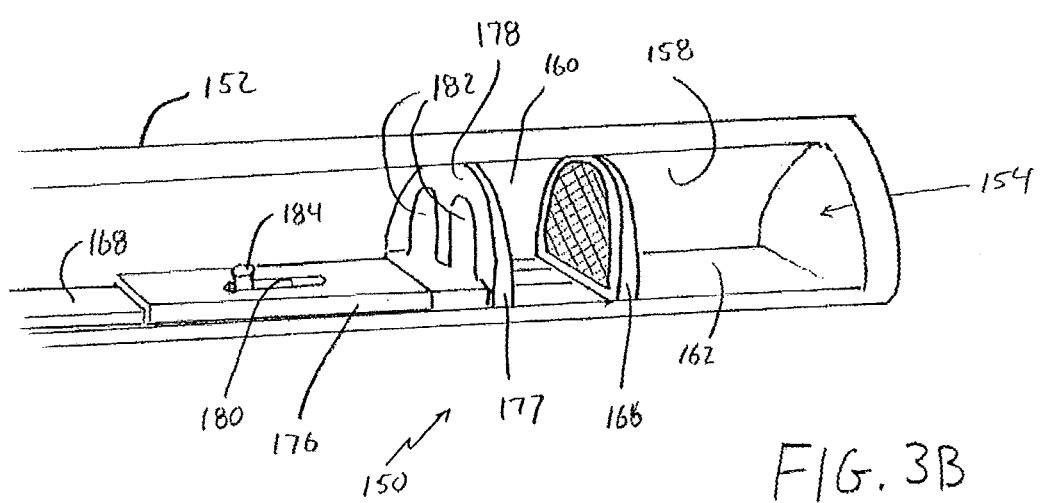
FIG. 3B is a perspective view similar to FIG. 3A, but illustrating the calculus removing/retrieving device when the sealing member is in a closed condition or state.

The second part 178 of the sealing member 164 possesses an outer surface 177 that matches the shape of the inner surface 158 of the tubular body 152. The outer surface 177 of the second part 178 thus contacts the inner surface 158 of the tubular body in a sealing manner. That is, the second part 178 of the sealing member 164, which can be in the form of a gasket, forms a seal with the inner surface 158 of the tubular body 152. The second part 178 of the sealing member 164 includes one or more spaced apart through holes 186. In the illustrated embodiment, the second part 178 of the sealing member 164 includes two through holes 186. The through hole(s) 186 preferably possess a shape that matches the outer shape of the upstanding cover elements 182. As described in more detail below, this allows the cover elements 182 to close, for example by covering or being positioned in, the through holes 186 in the second part 178 of the sealing member 164. FIG. 3B illustrates an example in which the cover elements 182 are positioned in the through holes 186 in the second part 178 of the sealing member 164 so that the sealing member 164 is in a closed state or condition.

A filter 166 is also fixed to the second part 178 of the sealing member 164 so that the filter 166 and the second part 178 of the sealing member 164 move together as a unit. The filter 166 is positioned axially between the second part 178 of the sealing member 164 and the retrieval space 162 in which calculus is collected (held) during the calculus retrieval operation as will be described in more detail below.

The plunger 168 includes an upstanding pin 184 that is positioned in the elongated slot 180 in the second part 176 of the sealing member 164. As described above, the first part 176 of the sealing member 164 is movable along the plunger 168 so that the first part 176 of the sealing member 164 and the second part 178 of the sealing member 164 are relatively axially movable. The tube 132 shown in FIG. 2 is connected to the closed end of the tubular body 152 so that a liquidtight arrangement exists in which fluid inside the tubular housing does not leak outside the tubular body by way of the tube 132.

FIG. 3A illustrates the first part 176 of the sealing member 164 at a position in which the first part 176 of the sealing member 164 is axially spaced farthest from the second part 178 of the sealing member 164. In this position, the upstanding pin 184 on the plunger 168 is located at the forward-most end of the elongated slot 180, and the cover elements 182 on the first part 176 of the sealing member 164 are spaced apart from the through holes 186 in the second part 178 of the sealing member 164. The through holes 186 in the second part 178 of the sealing member 164 are thus open. The first and second parts 176, 178 of the sealing member 164 are axially relatively movable towards one another until the cover elements 182 on the first part 176 of the sealing member 164 cover or, as illustrated in FIG. 3B, are positioned in the through holes 186 in the second part 178 of the sealing member 164.

When the first and second parts are positioned relative to one another in the manner illustrated in FIG. 3A, fluid is able to flow through the through holes 186. On the other hand, when the cover elements 182 are positioned in the through holes 186 as shown in FIG. 3B, the cover elements 182 cover the through holes 186 and prevent fluid from passing through the second part 178.

The operation of the embodiment illustrated in FIGS. 2, 3A and 3B is as follows. The calculus removing/retrieving device 150 is connected to an operating member, for example the operating member 30 shown in FIG. 1. The calculus removing/retrieving device 50 is then inserted into the living body and advanced to the location of the calculus to be retrieved and removed. This can be accomplished in the manner described above. When the inlet 156 of the tubular body 152 is positioned adjacent the calculus to be retrieved and removed, and with sealing member 164 of the calculus removing/retrieving device 50 arranged in a manner like that shown in FIG. 3A, the plunger 168 is axially moved in the rearward or proximal direction (by operating the operating member 30 which pulls the manipulation wire 33 and rearwardly moves the plunger 168). The rearward movement of the plunger 168 causes the second part 178 of the sealing member 164 to also move in the rearward or proximal direction, together with the filter 166. Initially, in a divided state of the sealing member 164, the second part 178 moves relative to the first part 176 of the sealing member 164, and the pin 184 moves rearwardly in the slot 180 so that the second part 178 approaches the first part 176. It is possible to hold the first part 176 of the sealing member 164 so that this relative movement occurs. The first part 176 and the plunger 168 can also be configured so that the friction between the first part 176 and the plunger 168 is relatively low so that such holding of the first part 176 may not be necessary. Also, the retrieval space 162 of the tubular body 152 contains, or is filled with, fluid (water/saline) and so both the first part 176 and the second part 178 receive the drag (resistance) of the fluid against moving. This resistance can function as a holding mechanism.

After the second part 178 of the sealing member 164 has moved relative to the first part 176 of the sealing member 164 over a first axial distance generally equal to the length of the elongated slot 180 in the first part 176 of the sealing member 164, the pin 184 contacts the proximal end of the slot 180. At about the same time, the upstanding cover elements 182 are positioned in or cover the through openings 186 in the second part 178 of the sealing member 164 as shown in FIG. 3B. When the sealing member 164 is in this integrated state in which the first and second parts 176, 178 of the sealing member move together, further rearward movement of the plunger 168 causes rearward movement of the first part 176 of the sealing member 164, the second part 178 of the sealing member 164 and the filter 166. The first part 176 of the sealing member 164, the second part 178 of the sealing member 164 and the filter 166 move together over a second axial distance until the first part 176 of the sealing member 164, the second part 178 of the sealing member 164 and the filter 166 reach the limit if the rearward movement. Because the second part 178 is in sealing contact with the inner surface 158 of the tubular body 152, the rearward movement of the second part 178 (while the through holes 186 in the second part 178 of the sealing member 164 are closed) causes calculus and fluid to be sucked into the interior 160 of the tubular body 152 by way of the inlet 154 so that the calculus (and fluid) is located in the retrieval space 162. At approximately the same time discharging of the fluid that has been introduced into the space between the proximal surface of the sealing member 164 and the closed end of the tubular body 152 by way of the outlet occurs, if the space between the proximal surface of the sealing member 164 and the closed end of the tubular body 152 has been filled by the fluid to some extent. The calculus removing/retrieving device 150 can be provided with a stop (e.g., similar to the push member 569 shown in FIGS. 14 and 15 and described below) to limit the rearward movement.

After calculus has been drawn into or sucked into the interior 160 of the tubular body 152 and the rearward movement of the plunger (as well as the first part 176 of the sealing member 164, the second part 178 of the sealing member 164 and the filter 166) is stopped, the plunger 168 is axially moved in the forward or distal direction (i.e., to the right in FIG. 3B). During a first part of the movement of the plunger in the axial direction (i.e., until the upstanding pin 184 on the plunger 168 contacts the distal or forward end of the elongated slot 180 in the second part 176 of the sealing member 164), the second part 178 of the sealing member 164 moves relative to and away from the first part 176 of the sealing member 164. The cover parts 182 thus move away from the through holes 186 in the second part 178 of the sealing member 164 so that the through holes 186 become uncovered (i.e., are once again open). During this first part of the movement of the plunger until the upstanding pin 184 on the plunger 168 contacts the distal or forward end of the elongated slot 180 in the second part 176 of the sealing member 164, the second part 178 of the sealing member 164 moves the first axial distance relative to first part 176 of the sealing member 164.

When the upstanding pin 184 on the plunger 168 contacts the distal or forward end of the elongated slot 180 in the second part 176, further axial movement of the plunger 168 in the forward or distal direction causes the second part 178 of the sealing member 164, the first part 176 of the sealing member 164 and the filter 166 to axially move together in the forward or distal direction over a second axial distance until the limit of the forward movement is reached. The calculus removing/retrieving device 150 can be provided with a stop (e.g., similar to the stop 580 shown in FIG. 14 and described below) to limit the forward movement. When the plunger 168 is pushed and axially moved in the forward or distal direction, the plunger does not create both suction and exhaust, but rather only the axial position of the plunger changes. Fluid in the retrieval part or retrieval space 162 is able to flow through the filter 166, flow past the through holes 186 in the second part 178 and reach the space between the proximal surface of the sealing member 164 and the closed end of the tubular body 152. While fluid is able to flow through the filter 166, the filter is specifically configured to prevent the passage of the calculus in the retrieval space 162. The calculus is thus retained in the retrieval space 162. In this illustrated and disclosed embodiment, when the sealing member 164 is in the open state or condition, fluid is not exhausted through the outlet. When the sealing member 164 is in the closed state or condition, fluid present in the space between the closed sealing member and the closed end of the tubular body (i.e., the closed left end of the tubular body as seen with reference to FIG. 2) can exhaust or flow out through the outlet(s) 156.

The plunger is then once again moved rearwardly in the proximal direction and the operation described above is repeated. This forward and rearward movement is repeated to continue drawing calculus into the interior of the tubular body to be retained in the retrieval space 162. Once the retrieval operation is complete, the calculus removing/retrieving device 150 is pulled out of the living body with the retrieved calculus remaining in the retrieval space 162.

The embodiment of the calculus removing/retrieving device shown in FIGS. 2, 3A and 3B does not specifically illustrate a barrier member at the inlet 156 of the tubular body. It is possible to use a barrier member, such as the barrier member shown in FIG. 1 and described above, or one of the barrier members described below.

Figure 4:
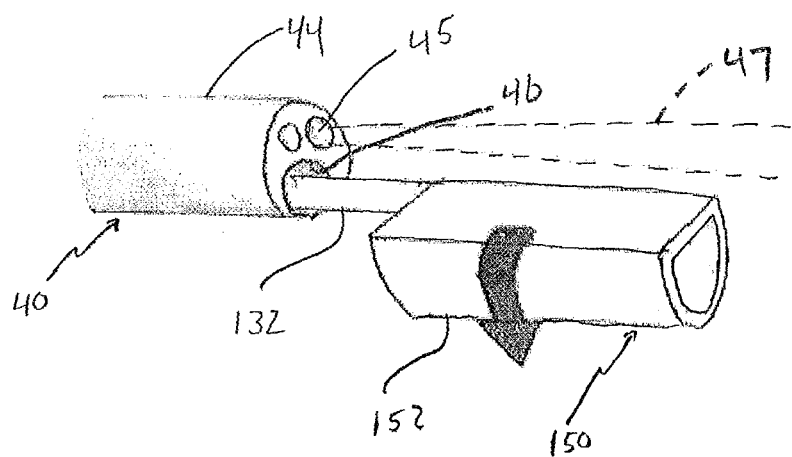
FIG. 4 is a perspective view of a calculus removing/retrieving device representing another example of the calculus removing/retrieving device disclosed here, illustrating one operational aspect of the device when used together with a ureteroscope.
Figure 5:
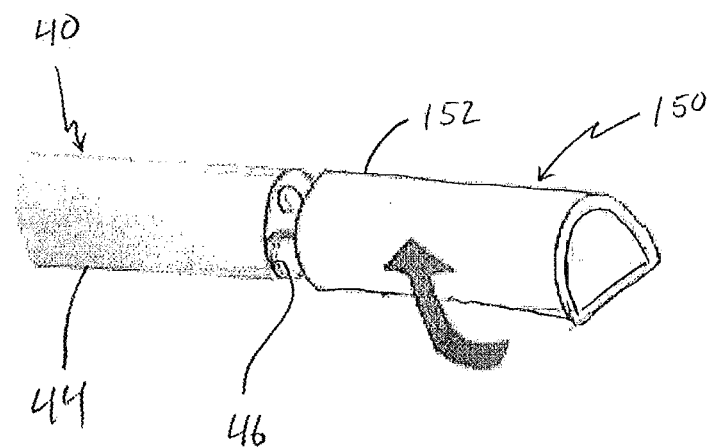
FIG. 5 is a perspective view of the calculus removing/retrieving device shown in FIG. 4, illustrating another operational aspect of the device when used together with a ureteroscope.

FIGS. 4 and 5 illustrate a variation on the embodiment illustrated in FIGS. 1-3B. In this embodiment, the tube 132 is rotationally fixed relative to the elongated tubular body 152. As a result, the tube 132 and the tubular body 152 rotate together as a unit when the tube 132 is rotated. This is beneficial from the following standpoint.

As illustrated in FIG. 4, the ureteroscope includes an objective lens 45 providing a field of view 47 (generally indicated in dotted outline in FIG. 4) during the calculus removing/retrieving operation. The tube 132 is offset from the central axis of the elongated tubular body 152. That is, the central axis of the tube 132 and the central axis of the tubular body 152 are not coaxial. Further, the central axis of the instrument channel 46 in the ureteroscope 40 is radially offset from the central axis of the distal end portion 44 of the ureteroscope 40. By virtue of this construction, it is possible to maintain visibility (i.e., to maintain unobstructed visibility or view) of the portion of the living body in front of the tubular body 152 during the calculus removing operation.

FIG. 4 illustrates the position or orientation of the tubular body 152 relative to the ureteroscope 40 during the calculus retrieval operation, while FIG. 5 illustrates the position or orientation of the tubular body 152 relative to the ureteroscope 40 during insertion of the calculus removing/retrieving device into the living body (lumen of the living body) and during withdrawal of the calculus removing/retrieving device from the living body (lumen of the living body). As the tubular body 152 is being introduced into the living body (into the lumen of the living body) and is being advanced in the living body (along the lumen of the living body) to the position in the living body at which calculus to be retrieved and removed is located, the tubular body 152 is positioned or oriented relative to the ureteroscope 40 in the manner illustrated in FIG. 5. In this position, the central axis of the tubular body 152 and the central axis of the ureteroscope (the distal portion of the ureteroscope 40 adjoining the tubular body 52) are aligned or are coaxial. This provides a relatively small and streamlined outer configuration that facilitates the introduction and movement of the tubular body and ureteroscope 40 into and long the living body (lumen of the living body).

After the tubular body 152 is located in the living body (lumen of the living body) at the position in the living body (lumen of the living body) at which calculus to be retrieved and removed is located, the tubular body 152 is rotated relative to the distal portion of the ureteroscope 40 in the direction indicated by the arrow in FIG. 4 so that the tubular body 152 rotates from the position shown in FIG. 5 to the position illustrated in FIG. 4. In this position shown in FIG. 4, the central axis of the tubular body 152 and the central axis of the ureteroscope (the distal portion of the ureteroscope 40 adjoining the tubular body 52) are not aligned (i.e., are not coaxial). With the tubular body 152 positioned in the manner shown in FIG. 4, the calculus retrieval operation can be carried out without obstructing the field of view 47 of the objective lens 45. After the calculus retrieval operation is completed as described earlier, the tubular body 152 is rotated relative to the distal portion of the ureteroscope 40 in the direction indicated by the arrow in FIG. 5 so that the central axis of the elongated body 152 and the central axis of the distal end portion of the ureteroscope 40 are once again aligned or coaxial with one another. This allows the tubular body 152 and the ureteroscope 40 to be more easily removed from the living body.

Figure 6:
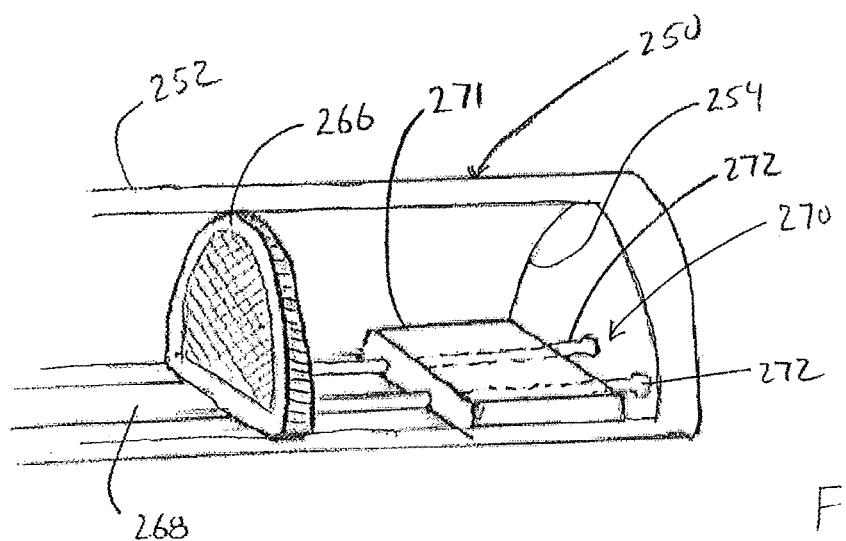
FIG. 6 is a perspective view of a calculus removing/retrieving device representing another example of the calculus removing/retrieving device disclosed here, illustrating one operational aspect of the device.
Figure 7:
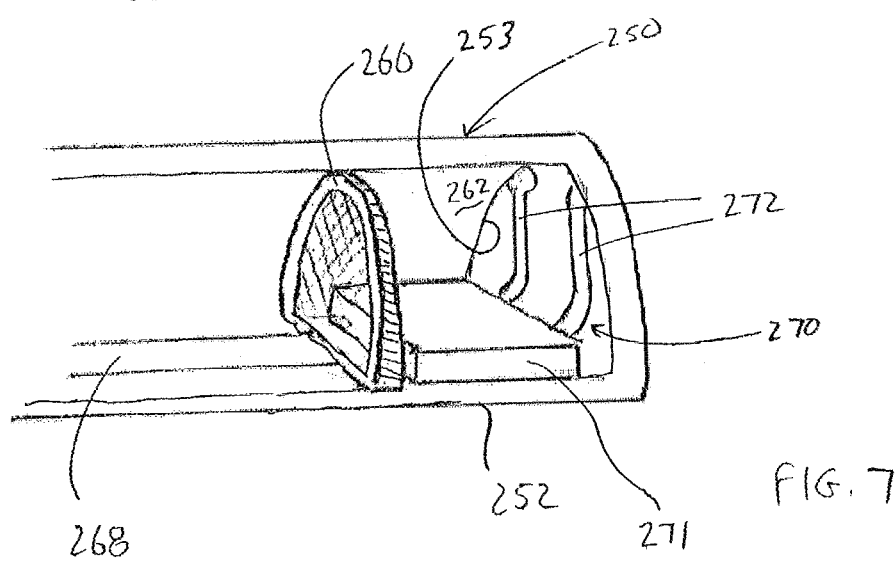
FIG. 7 is a perspective view of the calculus removing/retrieving device shown in FIG. 6, illustrating a different operational aspect of the device.

FIGS. 6 and 7 illustrate another embodiment of the calculus removing/retrieving device representing another example of the calculus removing/retrieving device and operational method disclosed here. Features in this embodiment which are similar to features described in earlier embodiments are identified by common referenced numerals, but preceded by a "2". A detailed description of features in this embodiment that are similar to features in the earlier embodiment is not repeated. The following detailed description focuses primarily on differences between this embodiment and the earlier embodiment. FIGS. 6 and 7 illustrate another version of a barrier member that can be provided at the inlet of the tubular body.

FIGS. 6 and 7 illustrate a calculus removing/retrieving device similar to the one shown in FIGS. 2 and 3, except that the calculus removing/retrieving device 250 shown in FIGS. 6 and 7 includes a barrier member 270. That is, the barrier member 270 illustrated in FIGS. 6 and 7 can be sued with the calculus removing/retrieving device 150 illustrated in FIGS. 2 and 3. The barrier member 270 illustrated in FIGS. 6 and 7 includes several spaced apart barriers 272 that are fixed to the filter 266 so that the filter 266 and the barriers 272 move together as a unit. Because the filter 266 is fixed to a part of the sealing member (e.g., the second part 178 of the sealing member 164 shown in FIG. 3), the barrier member 270 also moves together with the sealing member.

The barrier member 270 also includes a barrier holder 271. The barrier holder 271 is a plate-shaped element fixed to the interior of the tubular body 252. In the illustrated embodiment, the barrier holder 271 is fixed to the bottom surface of the tubular body 252. The barriers 272 are elongated rod-shaped elements that pass through respective through passages (e.g., holes or grooves) in the barrier holder 271. The barriers 272 are movable relative to the barrier holder 271.

The barriers 272 are configured such that in the absence of an applied force (internal or external), the barriers 272 exhibit the curved shape or configuration shown in FIG. 7. That is, when a sufficient portion of the length of the barriers 272 extends distally beyond the distal end of the barrier holder 271, the barriers 272 naturally or automatically curve upward to function as a barrier across the inlet 254 of the tubular body 252. On the other hand, when the barriers 272 are moved rearwardly in the proximal direction so that the naturally curved part of the barriers 272 is positioned in the barrier holder 271 as shown in FIG. 6, the barriers 272 deviate from their natural curved state and become straight by virtue force applied by the barrier holder 271. In this state or position shown in FIG. 6, the barriers 272 do not cross the inlet and do not serve as a barrier for the inlet.

The material forming the barriers 272 can be shape memory metal (e.g., NiTi wire) so that the barriers 272 naturally exhibit the curved shape or configuration shown in FIG. 7, yet are straightened when moved rearwardly inside the barrier holder 271 as shown in FIG. 6. It is also possible to use other spring-like material that tends to exhibit a natural curved shape or configuration when a force (external or internal force) is not applied to the barriers 272.

During use, when the sealing member 164 (first and second parts 176, 178 of the sealing member 164) is positioned in the manner shown in FIG. 3, the barriers 272 are positioned in the manner illustrated in FIG. 6. As the plunger 168 is moved in the forward or distal direction, the barriers 272 move in the forward or distal direction so that the barriers 272 extend distally beyond the distal end of the barrier holder 271. During this forward movement of the barriers 272, the barriers 272 curve in a direction causing the barriers 272 to cross the inlet 254. The barriers 272 are thus moved to the position shown in FIG. 7. In this FIG. 7 position, the barriers 272 prevent calculus which has previously been drawn into the retrieval space 262 from being ejected out through the inlet 254.

When the plunger and the sealing member are then moved in the rearward or proximal direction to draw or suck calculus into the interior of the elongated body, the barriers 272 are also moved in the same direction. The barriers 272 are thus pulled back into the barrier holder 271 as shown in FIG. 6 so that the inlet 254 is once again open, thus allowing calculus to be drawn or sucked into the interior of the tubular body 252.

Figure 8:
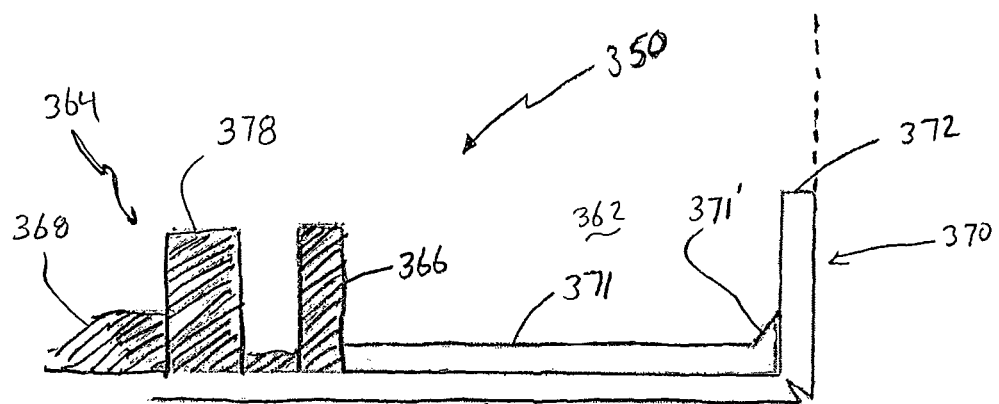
FIG. 8 is a perspective view of a calculus removing/retrieving device representing another example of the calculus removing/retrieving device disclosed here, illustrating one operational aspect of the device.
Figure 9:
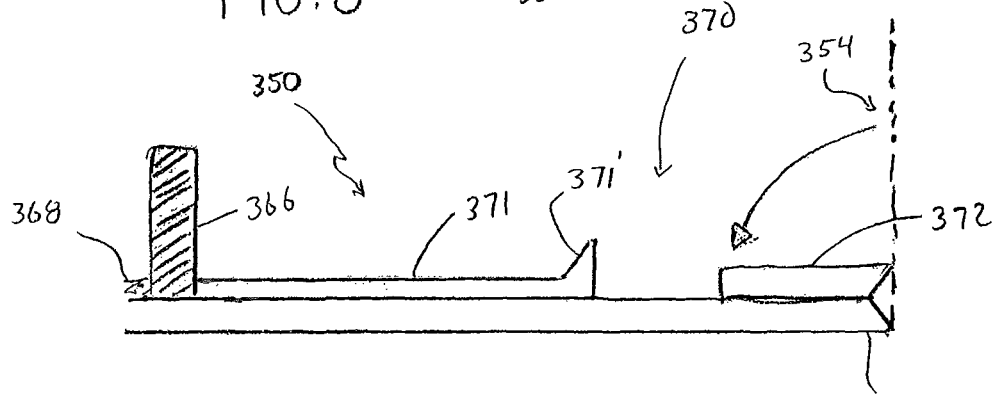
FIG. 9 is a perspective view of the calculus removing/retrieving device shown in FIG. 8, illustrating a different operational aspect of the device.

FIGS. 8 and 9 illustrate a further embodiment of the calculus removing/retrieving device representing another example of the calculus removing/retrieving device and operational method disclosed here. Features in this embodiment which are similar to features described in earlier embodiments are identified by common referenced numerals, but preceded by a "3". A detailed description of features in this embodiment that are similar to features in the earlier embodiment is not repeated. The following detailed description focuses primarily on differences between this embodiment and earlier embodiments. FIGS. 8 and 9 illustrate another version of a barrier member that can be provided at the inlet of the tubular body.

In this embodiment shown in FIGS. 8 and 9, the barrier member 370 is a hinged barrier 372 that is hinged to the bottom of the tubular body 352. That is, the barrier 372 is connected to the bottom of the tubular body 352 at a hinge. The barrier member 370 also includes a barrier holder 371 that is fixed to the filter 366 so that the filter 366 and the barrier holder 371 move together as a unit. Because the filter 366 is fixed to a part of the sealing member (e.g., the second part 378 of the sealing member 364 schematically depicted in FIG. 3), the barrier holder 371 also moves together with the sealing member. The distal end of the barrier holder 371 includes an enlarged stop 371' that serves as a stop to maintain the barrier 372 in the upright position shown in FIG. 8 when the stop 371' is pressing against (contacting) the barrier 372. In the illustrated embodiment, the enlarged stop 371' possesses a planar forward facing front surface that contacts the barrier 372.

The barrier 372 can be in the form of a wall that covers a sufficiently large portion of the inlet that calculus located in the retrieval space 362 is unable to flow out through the inlet 354 when the barrier is in the upright position shown in FIG. 8. Alternatively, the barrier 372 can be in the form of several spaced apart and hingedly connected upright wall portions that are each held in the upright position by a respective barrier holder 371 and stop 371'. In this alternative, the several spaced apart barriers would be configured (sized) to cover a sufficiently large portion of the inlet 354 that calculus located in the retrieval space 362 is unable to flow out through the inlet 354 when the barriers are in the upright position shown in FIG. 8.

When the filter 366 and the second part 378 of the sealing member 364 are positioned at the forward-most or distal-most position shown in FIG. 8, the stop 371' at the distal end of the barrier holder 371 acts against the barrier 372 to keep the barrier 372 in the upright position. In this position, the barrier 372 extends across the inlet 354 of the tubular body to close the inlet 354. When the plunger 368 is moved in the rearward or proximal direction (to the left in FIGS. 8 and 9) to move the filter 366 and the sealing member 364 in the rearward or proximal direction, the barrier holder 371 also moves in the rearward or proximal direction. The barrier(s) 372 is thus no longer held in the upright position by the stop 371'. As the sealing member 364 is moved in the rearward or proximal direction to draw calculus and fluid into the interior of the tubular member 352, the incoming calculus and fluid applies a force to the barrier 372 causing the barrier to fall or rotate in the direction indicated by the arrow in FIG. 9 so that the barrier 272 overlies the bottom of the tubular body 352 as illustrated in FIG. 9.

Figure 10:
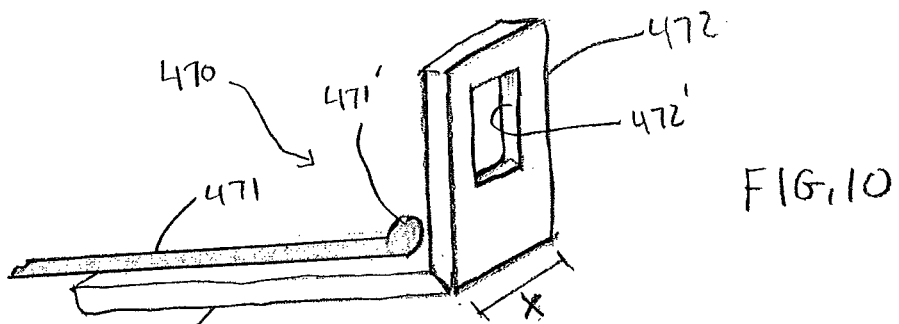
FIG. 10 is a perspective view of a calculus removing/retrieving device representing another example of the calculus removing/retrieving device disclosed here.
Figure 11:
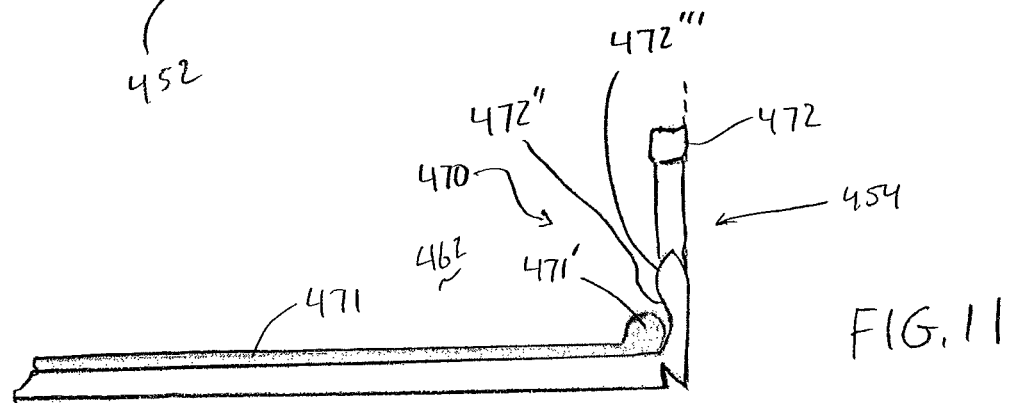
FIG. 11 is a perspective view of the calculus removing/retrieving device shown in FIG. 10, illustrating an operational aspect of the device.
Figure 12:
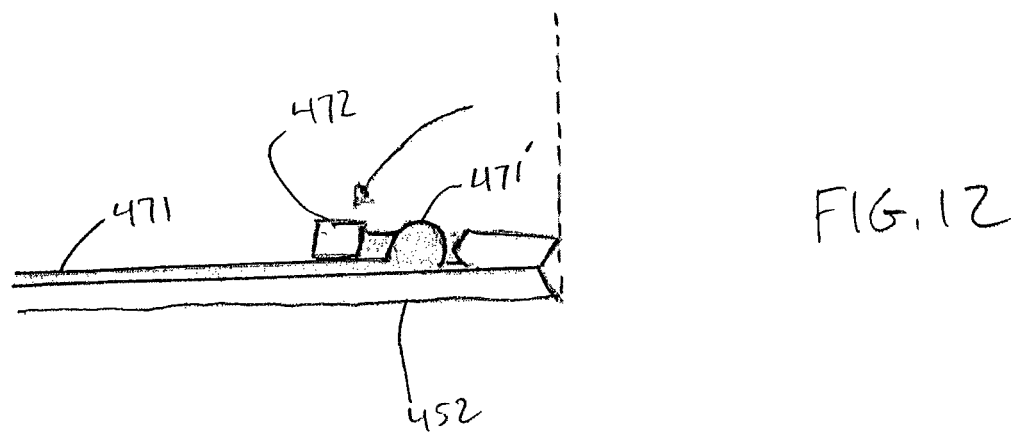
FIG. 12 is a perspective view of the calculus removing/retrieving device shown in FIG. 10, illustrating different operational aspects of the device when used together with a ureteroscope.

FIGS. 10-12 illustrate an embodiment of the calculus removing/retrieving device representing another example of the calculus removing/retrieving device and operational method disclosed here. Features of this embodiment which are similar to features described in the earlier embodiment are identified by common reference numerals, but preceded by a "4". A detailed description of features in this embodiment that are similar to features in the earlier embodiment is not repeated, and the following detailed description focuses primarily on differences between this embodiment and the earlier embodiment.

This embodiment shown in FIGS. 10-12 is similar to the embodiment illustrated in FIGS. 8 and 9, except that the configuration of the barrier member 470 is different. The barrier member 470 shown in FIGS. 10-12 includes a barrier 472 hingedly connected to the bottom wall of the tubular body and positioned at the inlet 454 of the tubular body 452. The barrier 472 includes a through opening 472'. The barrier member 470 also includes a barrier holder 471 that is fixed to the filter so that the barrier holder 471 moves together with the filter (and the second part of the sealing member as well as the plunger). The barrier member 470 extends forwardly in the distal direction towards the barrier 472. A stop 471' is positioned at the distal end of the barrier holder 471.

In this embodiment illustrated in FIGS. 10-12, the stop 471' is rounded. In addition, the barrier holder 471 is positioned in aligned relation to the through opening 472' in the barrier 472, considered with reference to the width-wise direction (i.e., the width-wise dimension indicated as "X" in FIG. 10). In the illustrated embodiment, the barrier holder 471 and the through opening 472' are both positioned generally in the center of the barrier 472 with reference to the width-wise dimension indicated X.

When the sealing member is in the forward most or distal-most position, the stop 471' contacts the barrier 472 to maintain the barrier 472 in the upright position as illustrated in FIG. 11. In this position, the stop 471' is positioned below the through opening 472'. As illustrated in FIG. 11, the surface of the barrier 472 facing towards the stop 471' possesses a concavo-convex shape. The concavo-convex shape includes a portion 472" possessing a concave shape and a portion 472''' possessing a convex shape. The concave portion 472" receives the stop 471' when the sealing member is in the forward-most or distal-most position with the stop 471' in contact with the barrier 472.

When the sealing assembly is positioned in the forward-most or distal-most position so that the barrier 472 is upright and the stop 471' is pushing-on and contacting the barrier 472, movement of the plunger and the sealing assembly in the rear or proximal direction causes the barrier holder 471 and the stop 471' to also move rearwardly or in the proximal direction. As discussed above, the rearward movement of the sealing member draws fluid and calculus into the interior of the tubular body through the inlet 454. This inflow of fluid and calculus causes the barrier 472 to rotate or pivot to the left in FIG. 11 so that the barrier 472 falls down to the position show in FIG. 12. In this position, the barrier 472 overlies the bottom of the tubular body 452 as illustrated in FIG. 12, and the inlet 454 of the tubular body 452 is open. In this position, the stop 471' is located in the window 472' as depicted in FIG. 12. The through opening or window 472' in the barrier 472 can be appropriately dimensioned to accommodate the maximum rearward movement of the stop 471' (sealing member/plunger) in the proximate direction. Aligning the stop 471' with the through opening 472' allows the enlarged stop 471' to be located in the through opening 472' when the barrier 472 is pivoted to the position shown in FIG. 12. This allows the barrier 472 to pivot further towards the bottom of the tubular body 452 than would otherwise be the case if the pivoting movement of the barrier 472 was limited by the stop 471'. In addition, this aligning enables the barrier 472 to open by a shorter stroke of stop 471 than is the case with the no-window type device (i.e., FIGS. 8 and 9). The short stroke helps improve and maximize the calculus removing/retrieving efficiency. Through a single pulling of the stop 471, the time required for opening the barrier 472 become less than the time for suction.

When the sealing member is moved in the forward or distal direction, the barrier holder 471 also moves in the forward or distal direction. This causes the stop 471' to push on the barrier 472 to raise the barrier 472 from the folded position (open state) illustrated in FIG. 12 to the upright position (closed state) illustrated in FIG. 11 in which the barrier 472 closes the inlet 452 so that calculus retrieved and held in the retrieval space 462 of the tubular body 452 does not flow out through the inlet 454. The rounded or curved shape of the stop 471' and the convex shape of the portion 472''' interact with one another to facilitate lifting of the barrier 472 from the folded position shown in FIG. 12 to the upright position illustrated in FIG. 11 when the barrier holder 471 and the stop 471' are moved in the forward or distal direction during movement of the plunger in the forward or distal direction. The manner of operation of this embodiment is similar to that described above and so such description is not repeated.

As discussed above, the window or through opening 472' in the barrier 472 shown in FIGS. 10-12 allows the barrier 472 to be further folded away from the inlet 454 than would otherwise be the case in the absence of the window or through opening 472'. The through opening 472' enables the barrier 472 to open by a shorter stroke of the stop 471 than is the case with the no-window type device (i.e., FIGS. 8 and 9). The shorter stroke imparts calculus removing/retrieving efficiency to the device. Through a single pulling of the stop 471, the time required for the opening the barrier 472 is less than the time for suction. The through opening 472' also allows fluid in the retrieval space 462 to flow out when the barrier holder 471 and the stop 471' are moved in the forward or distal direction.

FIGS. 13-15 illustrate an additional embodiment of the calculus removing/retrieving device representing another example of the calculus removing/retrieving device and operational method disclosed here. Features of this embodiment which are similar to features described in the earlier embodiment are identified by common reference numerals, but preceded by a "5". A detailed description of features in this embodiment that are similar to features in the earlier embodiment is not repeated, and the following detailed description focuses primarily on differences between this embodiment and the earlier embodiment.

Referring to FIG. 13, the calculus removing/retrieving device 550 includes a tubular body or elongated member 552 having an inlet 554 and an outlet 556. In the illustrated embodiment, the tubular body 552 is provided with a plurality of outlets 556. Also, in this illustrated embodiment of the calculus removing/retrieving device, the tubular body is a circular cylindrical tubular body, though it is to be understood that the tubular body can have tubular shapes other than a tubular cylindrical shape. A plunger 568 is connected to a sealing member 564, and the sealing member 564 is comprised of a first part 576 and a second part 578. The outer circumferential (annular) surface of the sealing member 564 (i.e., the outer circumferential surface of the first part 576 and the outer circumferential surface of the second part 578) contacts the inner surface of the tubular body 552 so that a seal is formed. A filter 566 is fixed to the second part 578 so that the second part 578 and the filter 566 move together as a unit. As illustrated in FIGS. 13 and 15A-15D, the filter 566 includes a plurality of through holes 567, and the second part 578 of the sealing member 564 includes a centrally located through hole 579 that communicates with the through holes 567 in the filter 566. So long as the through hole 579 in the second part 578 remains open, fluid flowing through the through holes 567 in the filter pass through the through hole 579 in the second part 578 of the sealing member.

Figure 15A:
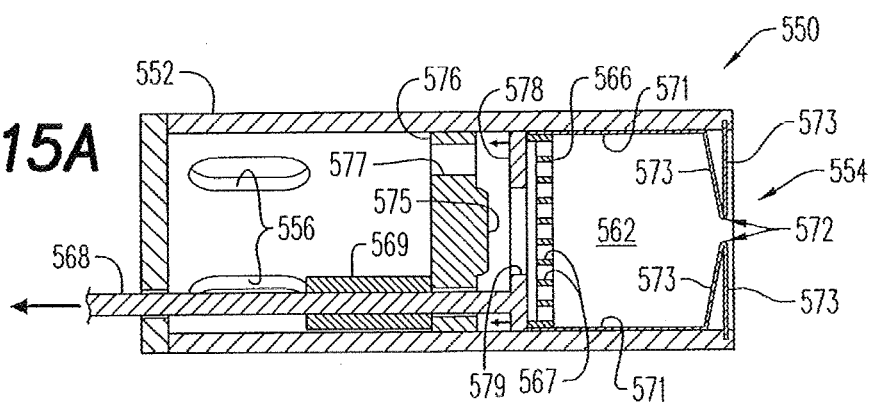
FIGS. 15A-15D are longitudinal cross-sectional views of the calculus removing/retrieving device shown in FIG. 13 illustrating various aspects of the operation of the device or method of using the device.
Figure 15B:
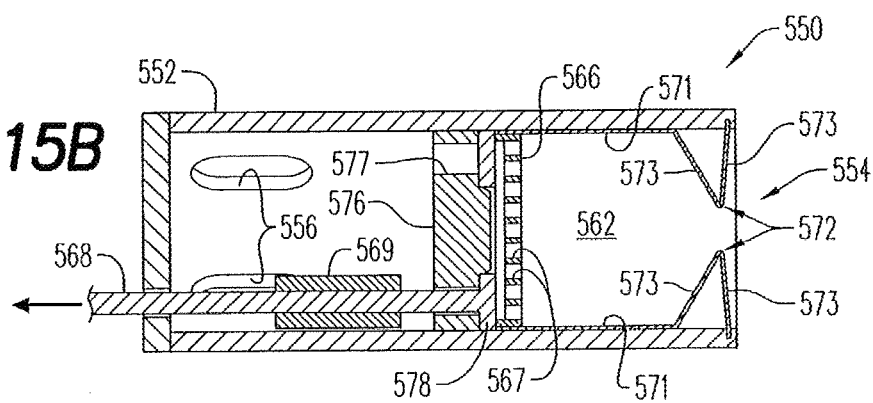
Figure 15C:
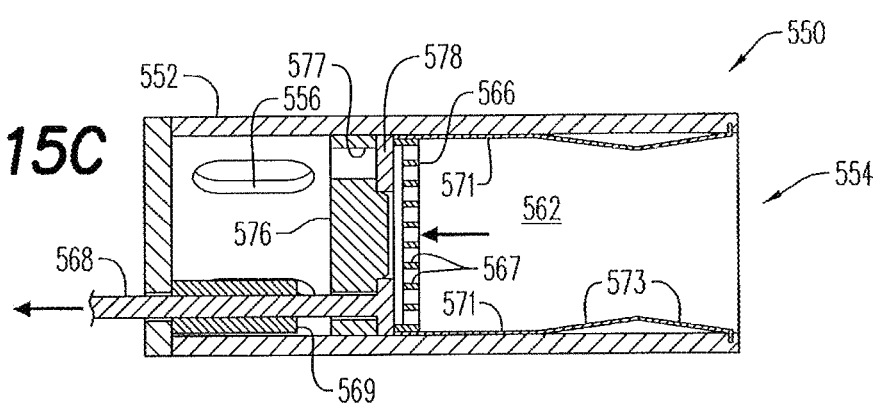
Figure 15D:
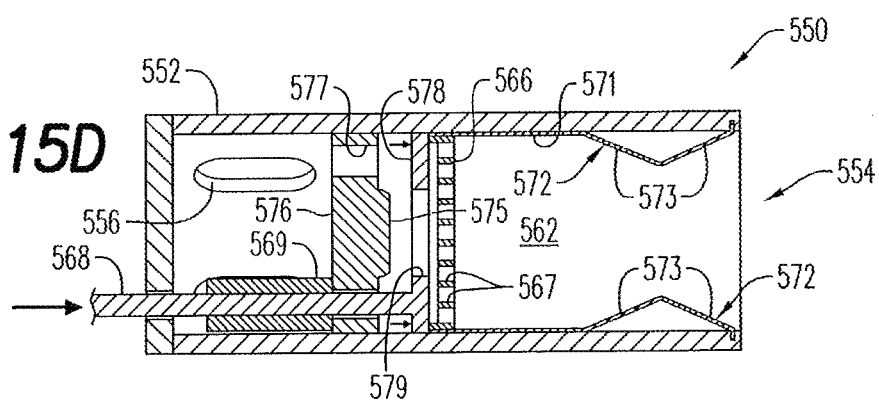

The first part 576 of the sealing member 564 includes a centrally located protrusion or projection, and a plurality of through holes 577 that are circumferentially spaced apart at positions radially outwardly of the projection 575. The first part 576 of the sealing member 564 is movable relative to the second part 578 (and relative to the filter 566) of the sealing member 564. In this way, the first part 576 and the second part 578 can be axially spaced apart from one another in the manner shown in FIG. 13 so that the central projection 575 of the first part 576 of the sealing member 564 is not positioned in (i.e., is axially spaced from) the through hole 579 of the second part 578 of the sealing member 564 as shown in FIGS. 15A and 15D. In this state (open state), fluid is able to pass through the through holes 567 in the filter 566, pass through the through hole 579 in the second part 578 of the sealing member 564 and pass through the through holes 577 in the first part 576 of the sealing member 564 so that strong fluid flow is not generated enough to suck the stones and to exhaust the stones gathered into retrieval space 562.

In this open state of the sealing member 564, fluid is not exhausted through the outlet(s) 556. On the other hand, the first part 576 and the second part 578 of the sealing member 564 can be relatively axially moved so that the facing surfaces of the first and second parts 576, 578 directly contact one another as illustrated in FIGS. 15B and 15C. In this state, the projection 575 on the first part 576 is positioned in the through hole 579 in the second part 578, and so the fluid path through the second part 578 of the sealing member 564 is closed off. In this closed position of the sealing member 564, fluid flows into the retrieval space 562 by way of the inlet 554, and fluid between the sealing member 564 and the closed end of the tubular housing 552 exits through the outlet(s) 556.

The plunger 568 passes freely through the first part 576 of the sealing member 564 and is fixed to the second part 578 of the sealing member 564. The plunger 568 and the second part 578 of the seal member thus move together as a unit. A push member 569 is fixed to the plunger 568 so that the plunger 568 and the push member 569 move together as a unit. With this construction, beginning from the position illustrated in FIG. 13 and FIG. 15A, when the plunger 568 is moved in the proximal or rearward direction represented by the arrow in FIG. 15A (i.e., to the left in FIGS. 13 and 15A), the second part 578 of the sealing member 564 (and the filter 566) axially move relative to and towards the first part 576 of the sealing member 564. The first and second parts 576, 578 of the sealing member 564 will then contact each other as illustrated in FIG. 15B, and so further rearward pulling of the plunger 568 causes the entire sealing member 564 (i.e., the first part 576 ad the second part 578), as well as the filter 566, to move rearwardly in the proximal direction represented by the arrow in FIG. 15B (i.e., to the left in FIGS. 13 and 15B). Then the sealing member 564 reaches the end of its axial movement stroke in the proximal direction such as shown in FIG. 15C. After that, for the purpose of obtaining the next suction fluid flow, the plunger 568 is moved in the forward or distal axial direction represented by the arrow in FIG. 15D. During the initial part of this forward movement of the plunger, the second part 578 of the sealing member 564 moves relative to and away from the first part 576 of the sealing member 564 so that the projection 575 on the first part 576 of the sealing member 564 moves out of the through hole 579 in the second part 578 of the sealing member 564. The first and second parts 576, 578 of the sealing member 564 are thus axially spaced apart from one another. When the push member 569 contacts the first part 576 of the sealing member 564, the first and second parts 576, 578 of the sealing member 564, as well as the filter 566, move together in the forward or distal direction, and the axial spacing between the first and second parts 576, 578 of the sealing member 564 is maintained until the plunger reaches the end of its forward axial movement stroke. The forward axial movement stroke is limited by the contact between an elongated slot 580 and a proximal end surface (closed end surface) of the tubular body 552. The position of the slot 580 along the plunger 568 defines the limit of the forward axial movement. It is possible to configure the slot 580/plunger 568 so that the position of the slot 580 along the plunger 568 is adjustable, thus allowing adjustment of the forward axial movement limit.

The calculus removing/retrieving device 550 shown in FIG. 13 further includes a barrier member 570. The barrier member 570 includes a plurality of barriers or cover members 572. Each of the cover members 572 includes a pair of disks 573, 573 that are connected in a hinged manner to each other in a hinged manner. This hinged connection allows the disks 573, 573 to be positioned in a relative overlapping arrangement such as shown in FIG. 15A and in a spread out manner. Each of the barriers or covers 572 further includes a connector 571 connecting each respective barrier 572 to the filter 566 as illustrated in FIGS. 15A-15D. When the plunger 568 is axially moved in the proximal direction to also axially move the filter 566 (and the second part 578 of the sealing member 564) in the proximal direction away from the inlet 554, the barrier member 570 shifts from the position illustrated in FIG. 15A in which the barrier member 570 is closed to the position illustrated in FIG. 15C in which the barrier member 570 is opened.

As described above, each of the barriers 572 includes a pair of cover elements or disks 573, 573. The disk 573 in each pair which is closest to the inlet 554 (farthest from the filter 566) is preferably connected to the outer end or rim of the tubular body 552. Also, when the filter moves in the forward or distal direction after having been pulled rearwardly, the barrier member 570 shifts from the open configuration illustrated in FIG. 15D to the closed configuration illustrated in FIG. 15A.

The operation of the embodiment of the calculus removing/retrieving device 550 shown in FIGS. 13, 14 and 15A-15D is as follows. The device is positioned in the living body in the manner described above so that the inlet 554 of the tubular body 552 is located adjacent calculus to be retrieved and removed from the living body. At this time, the calculus removing/retrieving device 550 is in the operational condition shown in FIG. 15A. The plunger 568 is then pulled rearwardly in the proximal direction indicated by the arrow in FIG. 15A to axially move the filter 566 and the second part 578 of the sealing member 564 relative to and towards the first part 576 of the sealing member 564. During this relative movement, the first part 576 of the sealing member 564 preferably does not move. The second part 578 of the sealing member 564 eventually contacts the first part 576 of the sealing member 564 as illustrated in FIG. 15B. When this occurs, the projection 575 on the first part 576 of the sealing member 564 is positioned in the central through hole 579 in the second part 578 and so fluid flow through the first and second parts 576, 578 of the sealing member 564 is blocked or prevented. During this movement of the second part 578 of the sealing member 564 and the filter 566 in the rearward or proximal direction (i.e., from the position shown in FIG. 15A to the position shown in FIG. 15B), the barrier member 570 begins to shift from the closed position shown in FIG. 15A toward the open position shown in FIG. 15B. Thus, between the position illustrated in FIG. 15A and the position illustrated in FIG. 15B, the second part 578 of the sealing member 564 moves relative to the first part 576 of the sealing member 564 over a first axial distance.

Further axial movement of the plunger 568 in the rearward or proximal direction causes the sealing assembly 564 (i.e., the first part 576 and the second part 578) as well as the filter 566 to also move in the rearward or proximal direction. This causes the barrier member 570 to be shifted to the open condition illustrated in FIG. 15C. During this rearward movement of the sealing member 564, the passage of fluid through the sealing member 564 is blocked, so that the calculus removing/retrieving force is generated and calculus and fluid are drawn into the retrieving space 562 in the interior of the tubular body 552 by way of the inlet 554. Almost at the same time, the fluid in the space between the sealing member 564 and the inner bottom (closed end) of the tubular body 552 is exhausted by way of the outlet(s) 556. The volume of exhausted fluid is almost same as the migration volume of the first part 576. The calculus is able to enter the interior of the tubular body 552 because the barrier member 570 has shifted to the open position shown in FIG. 15C. FIG. 15C illustrates the calculus removing/retrieving device 550 after the plunger 568 has reached the end of its rearward axial movement in the proximal direction. Between the position illustrated in FIG. 15B and the position illustrated in FIG. 15C, the first and second parts 576, 578 of the sealing member 564 axially move a second axial distance that is greater than the first axial distance discussed above.

After the sealing member 564 reaches the end of its rearward movement in the proximal direction, the plunger 568 is pushed in the forward or distal direction. This causes the filter 566 and the second part 578 of the sealing member 564 to axially move together in the forward or distal direction so that the filter 566 and the second part 578 of the sealing member 564 move together from the position shown in FIG. 15C toward the position shown in FIG. 15D. During this movement, the barrier member 570 begins to shift from the open position shown in FIG. 15C, to the position shown in FIG. 15D and toward the closed position shown in FIG. 15A. During the initial movement of the plunger 568 in the forward or distal direction, the second part 578 of the sealing member 564 and the filter 566 move relative to and away from first part 576 of the sealing member 564 so that the second part 578 of the sealing member 564 become separated from the first part 576 of the sealing member 564. The projection 575 on the first part 576 of the sealing member 564 thus moves out of through hole 579 in the second part 578 of the sealing member 564 so that fluid is allowed to flow through the filter 566, through the through hole 579 in the second part 578 and through the through holes 577 in the first part 576 of the sealing member 564. Further forward movement of the plunger 568 causes the push member 569 to contact the first part 576 of the sealing member 564 as illustrated in FIG. 15D. Between the position illustrated in FIG. 15C and the position illustrated in FIG. 15D, the second part 578 of the sealing member 564 moves relative to the first part 576 of the sealing member 564 over a first axial distance that is the same as the first axial distance discussed above (i.e., the first axial distance between the position in FIG. 15A and the position in FIG. 15B).

As the plunger 568 moves in the forward direction, relatively weak fluid flow is generated to flow out through the inlet 564. But because the barrier member 570 is shifting toward the closed position, calculus that has been retrieved in the retrieval space 562 and that is held in the retrieval space does not flow out through the inlet 554 because the barrier member 570 blocks the calculus. In the illustrated embodiment, the barrier member 570 does not cover the entirety of the inlet. Rather, the barrier member 570 covers enough of the inlet 554 to prevent calculus from being discharged through the inlet and expelled outside the device during the forward axial movement of the plunger (and the sealing member 564), while permitting fluid to be discharged past the barrier member 570 at the inlet 554.

From the position illustrated in FIG. 15D, further forward movement of the plunger 568 causes the entire sealing member 564 (i.e., the first and second parts 576, 578 of the sealing member 564) as well as the filter 566 to move together in the forward or distal direction indicated by the arrow in FIG. 15D. As the operation of the calculus removing/retrieving device 550 shifts from the position shown in FIG. 15D toward the position shown in FIG. 15A, the barrier member 570 shifts to the closed position shown in FIG. 15A. Between the position illustrated in FIG. 15D and the position illustrated in FIG. 15A, the first and second parts 576, 578 of the sealing member 564 axially move a second axial distance that is greater than the first axial distance discussed above.

After the sealing member 564 reaches the end of its distal movement in the forward direction, the plunger 568 is once again moved in the rearward or proximal direction and the operation described above is repeated. It is thus possible to repeatedly draw or suck calculus into the interior of the tubular body 552 and to retain such calculus in the retrieval space 562. After the retrieval of the desired calculus is completed, the calculus removing/retrieving device 550 can be removed from the living body, thus removing the calculus from the living body.

FIGS. 16 and 17A-17D illustrate a further embodiment of the calculus removing/retrieving device representing another example of the calculus removing/retrieving device and operational method disclosed here. Features of this embodiment which are similar to features described in the earlier embodiments are identified by common reference numerals, but preceded by a "6". A detailed description of features in this embodiment that are similar to features in earlier embodiments is not repeated, and the following detailed description focuses primarily on differences between this embodiment and the earlier embodiment.

Referring initially to FIG. 16 the calculus removing/retrieving device 650 includes an elongated member or tubular body 652 having an inner surface 658 surrounding an interior 660 within the tubular body 652. In this illustrated embodiment, the tubular body is a circular cylindrical tubular body, but the tubular body can have other tubular shapes other than a cylindrical-shape. The tubular body 652 includes an inlet 654 and an outlet 656. In the illustrated embodiment, the outlet 656 is comprised of a plurality of circumferentially spaced apart outlets 656. Any desired number of outlets can be provided. The calculus removing/retrieving device 650 can be outfitted with a barrier member and a filter like those described above and shown in the drawing figures to achieve favorable results similar to those described above.

The calculus removing/retrieving device 650 also includes a sealing member 664. In this embodiment the sealing member 664 is a foldable sealing member that includes two seal parts 690, 692. The two seal parts include a first seal part 690 and a second seal part 692 that are foldable relative to one another to move between a folded state in which the two parts overlap or overlie one another and a spread state in which the two seal parts 690, 692 are spread-out and lie in a common plane.

The sealing member 664 also includes two axles 694, 696. The two axles include a first (proximal) axle 694 and a second (distal) axle 696. The first seal part 690 and the second seal part 692 are both rotatably mounted on the first axle 694 so that the first and second seal parts 690, 692 rotate about a common axis which, in this illustrated embodiment, is the axis of the first axle 694. The second axle 696 is connected to the first seal part 690 by way of a pair of arms or links 691. The second axle 696 is also connected to the second seal part 692 by way of a pair of arms or links 693. One of the arms 691 is fixed to the second axle 696 so that the arm rotates together with the second axle 696, while the other arm 691 is fixed to the first seal part 690 to rotate together with the first seal part 690.

The second axle 696 is also connected to the second seal part 692 by way of a pair of arms or links 693. One of the arms 693 is fixed to the first axle 696 while the other arm 693 is fixed to the second seal part 692 to move together with the second seal part 692.

The plunger 668 possesses a distal end that is fixed to the first axle 696 as illustrated in FIG. 16. The first axle 694 is comprised of two spaced apart axle parts 694', 694". The two axle parts 694', 694" include a lower axle part 694' and an upper axle part 694".

Figure 17A:
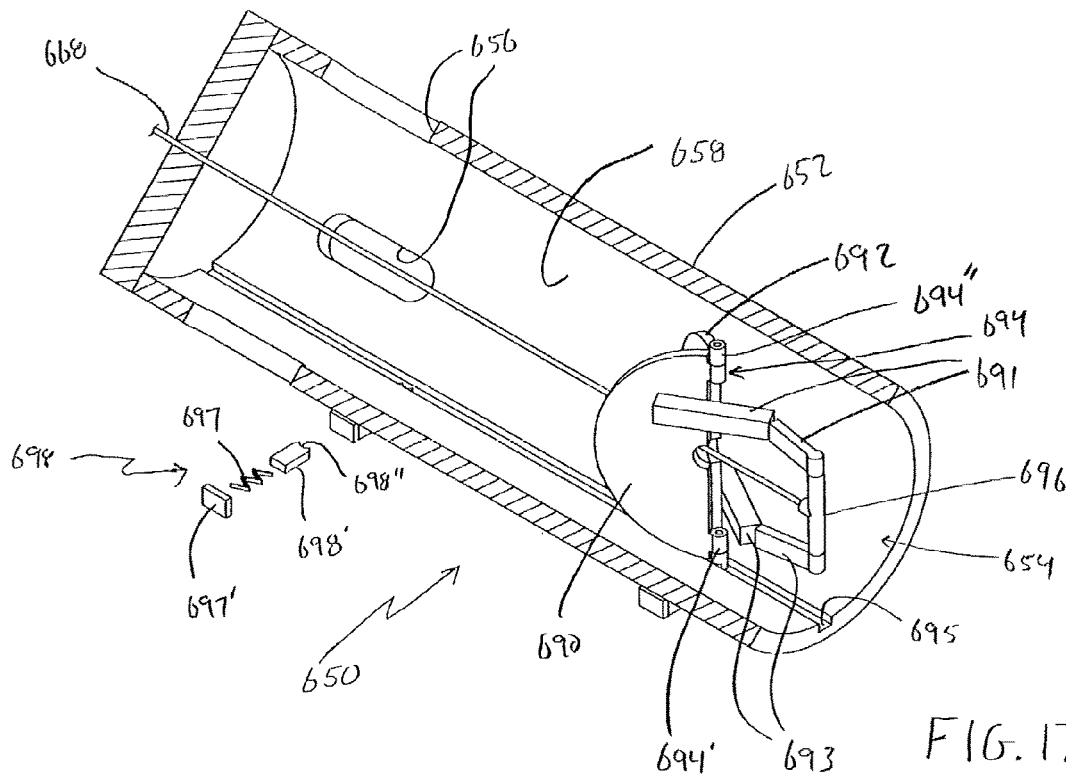
FIG. 17A is a perspective view of the calculus removing/retrieving device shown in FIG. 16 with the sealing member positioned at the distal end of its movement stroke in the tubular body while the sealing member is in the folded or open position.

Referring to FIG. 17A, the bottom interior surface of the tubular body 652 is provided with a groove 695 that preferably extends along the entire axial or longitudinal extent of the tubular body 652. The lower end of the first axle 694 (i.e., the lower axle part 694') is always positioned in the groove 695. When the sealing member 664 moves axially within the interior of the tubular body 652 as described in more detail below, the second axle 694 (lower axle part 694') is guided along the groove 695. The second axle 696 need not be positioned in the groove 695. More preferably though, both the first axle 694 and the second axle 696 are positioned in the groove 695 to stabilize the axial mobility and movement of the sealing member 664, but the second axle 696 is configured so that the second axle does not engage a proximal latch 698 and does not engage a distal latch 699 (for example the outer diameter of the second axle 696 is smaller than the outer diameter of the first axle 694). In addition, for purposes of stabilizing the axial mobility, a second groove can be provided in the interior surface of the tubular body 652 at a position opposite (diametrically opposed) to the groove 695. It is also possible to provide the top interior surface of the tubular body 652 with a groove similar to the groove 695 that preferably extends along the entire axial or longitudinal extent of the tubular body 652. The upper end of the first axle 694 (i.e., the upper axle part 694") can be positioned in this groove 695 at the top interior surface of the tubular body 652 and moves along such groove when the sealing member 664 moves axially within the interior of the tubular body 652. The upper end of the second axe can also be located in and move along this groove 695 at the top interior surface of the tubular body 652.

As illustrated in FIGS. 16 and 17A-17D, the proximal latch 698 and the distal latch 699 are mounted on the interior of the tubular body 652. These latches 698, 699 are configured to engage the proximal axle 694 (lower axle part 694') when the sealing member 664 is positioned at the distal end or proximal end of its axial travel extent. Specifically, the latches 698, 699 are configured to engage and hold the proximal axle 694 (lower axle part 694') until a sufficient pulling or pushing force applied by the plunger 668 overcomes the holding force of the latch 698, 699.

FIGS. 17A-17D provides a somewhat schematic illustration of one example of the proximal latch 698. The distal latch 699 can be similarly configured and so the following description of features and operation of the proximal latch 698 applies equally to the distal latch 699. The latch generally includes a plate-shaped member 698' provided with a curved groove or recess 698" at its forward end. A spring 697 acts in opposition to a stop 697' and applies a biasing force that urges the plate 698' in the forward direction indicated by the arrow in FIGS. 17A and 17B (i.e., toward the groove 695. The curved recess 698" is configured to receive the proximal axle 694 (lower axle part 694'). By appropriately selecting the depth of the curved recess 698" and the biasing force of the spring 697, it is possible to set the force, applied by the plunger 668, at which the proximal axle 694 (lower axle part 694') is released from the curved recess 698".

The operation of the embodiment of the calculus removing/retrieving device shown in FIGS. 16 and 17A-17D is as follows. To start, the calculus removing/retrieving device 650 is positioned in the living body in the manner described above so that the inlet 654 of the tubular body 652 is located adjacent calculus to be retrieved and removed from the living body. When the calculus removing/retrieving device 650 is positioned adjacent the calculus, the calculus removing/retrieving device 650 is arranged generally in the manner illustrated in FIG. 17A. In this position the distal axle 696 is axially spaced distally from the proximal axle 694, and the first and second seal parts 690, 692 are generally folded towards one another so that the sealing member is in the open position. In addition, when the sealing member 664 is in the distal-most axial position shown in FIG. 17A, the proximal axle 694 (lower axle part 694') is located in the groove 695 and is held by the distal latch 699.

Figure 17B:
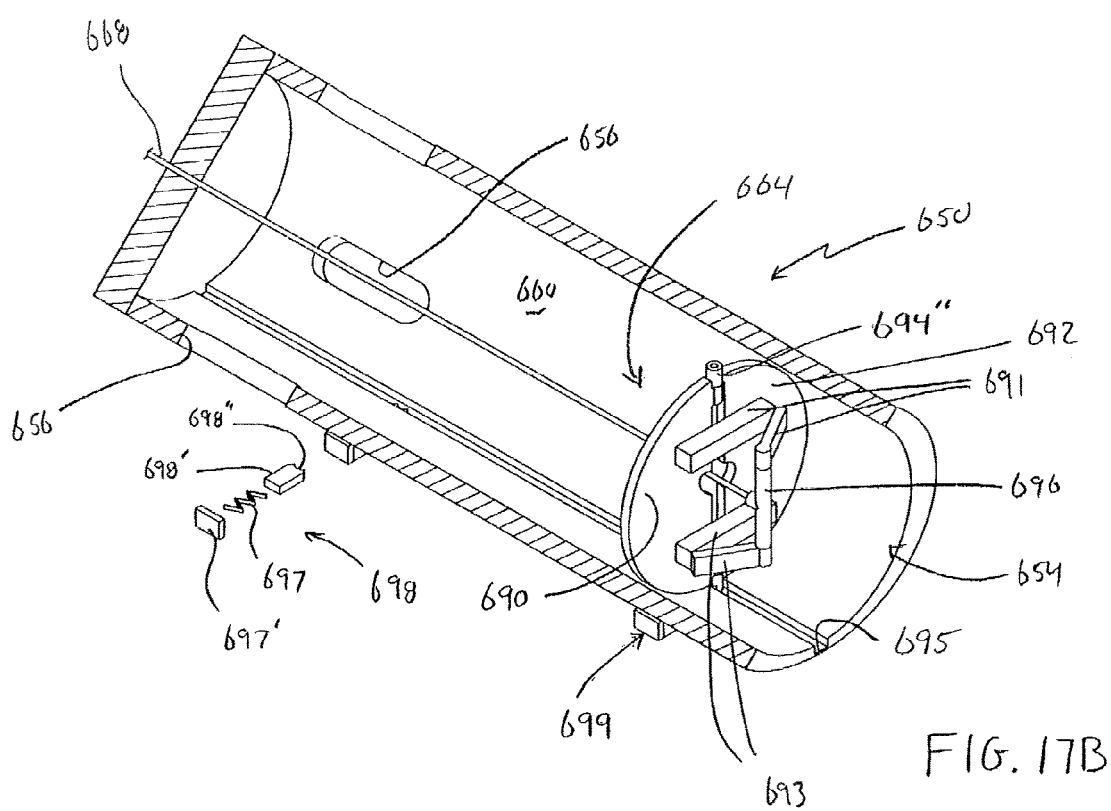
FIG. 17B is a perspective view of the calculus removing/retrieving device shown in FIG. 16 with the sealing member positioned at the distal end of its movement stroke in the tubular body while the sealing member is in the spread or closed position.
Figure 17C:
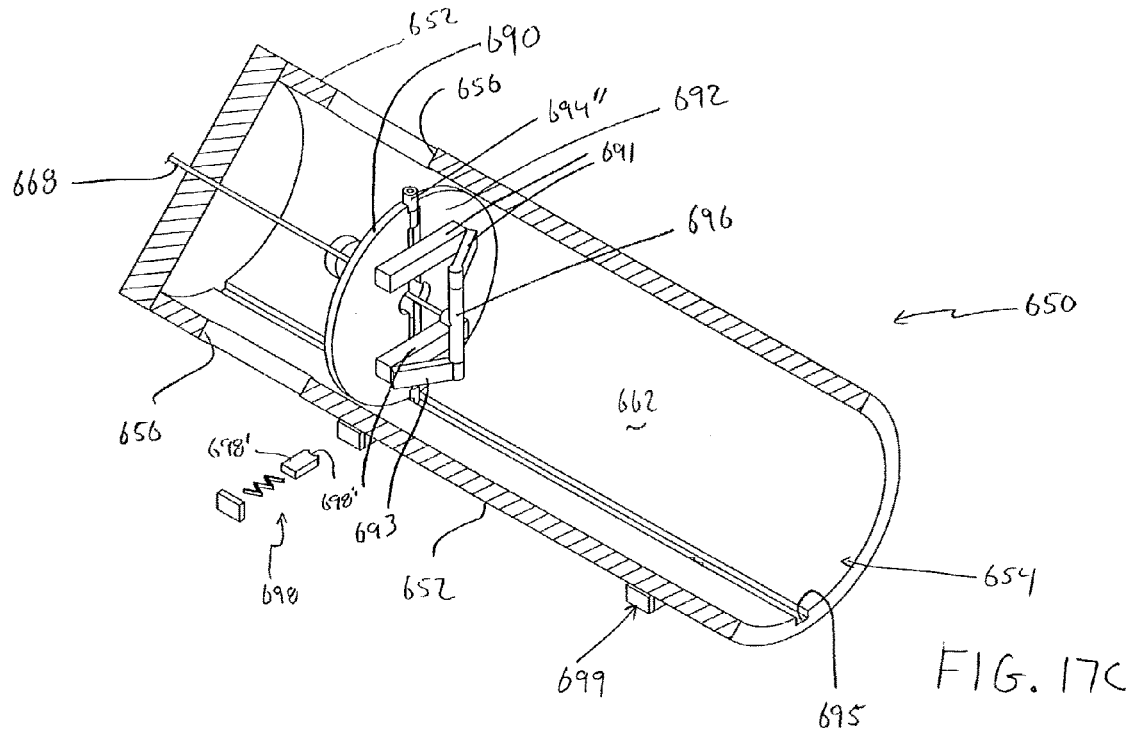
FIG. 17C is a perspective view of the calculus removing/retrieving device shown in FIG. 16 with the sealing member positioned at the proximal end of its movement stroke in the tubular body while the sealing member is in the closed or spread position.

Pulling the plunger 668 in the rearward or proximal direction causes the distal axle 696 to move axially toward and relative to the proximal axle 694. At this time, proximal axle 694 remains held in the distal latch 699 and does not axially move. As the distal axle 696 approaches the proximal axle 694, the configuration of the arms 691, 693 causes the first and second seal parts 690, 692 to rotate about the axis of the proximal axle 694 so that the first and second seal parts 690, 692 spread-out as illustrated in FIG. 17B. The sealing member 664 is thus shifted from the folded position shown in FIG. 17A to the spread position (closed position) depicted in FIG. 17B.

In the closed position shown in FIG. 17B, the outer peripheral surfaces of the first and second seal parts 690, 692 contact the inner surface 658 of the tubular body 652 to form a seal contact. As the sealing member moves from the spread-out position or closed position (i.e., the position shown in FIG. 17B) toward the folded position or open position (i.e., the position shown in FIGS. 17A and 17D), the contact area between the outer peripheral surface of the sealing member and the inner surface 658 of the tubular body 652 (i.e., the contact area between the outer peripheral surfaces of the first and second seal parts 690, 692 and the inner surface 658 of the tubular body 652) decreases. As the sealing member moves from the folded position or open position (i.e., the position shown in FIGS. 17A and 17D) toward the spread-out position or closed position (i.e., the position shown in FIG. 17B), the contact area between the outer peripheral surface of the sealing member and the inner surface 658 of the tubular body 652 (i.e., the contact area between the outer peripheral surfaces of the first and second seal parts 690, 692 and the inner surface 658 of the tubular body 652) increases. The maximum contact area between the outer peripheral surface of the sealing member and the inner surface 658 of the tubular body 652 occurs when the sealing member 664 is in the spread-out position or closed position (i.e., the position shown in FIG. 17B), while the minimum contact area between the outer peripheral surface of the sealing member and the inner surface 658 of the tubular body 652 occurs when the sealing member 664 is in the folded position or open position (i.e., the position shown in FIGS. 17A and 17D). Also, the contact area between the outer peripheral surface of the sealing member 664 and the inner surface of the tubular body 652 is relatively large while moving the sealing member 664 in the proximal direction and is relatively small when moving the sealing member 664 in the distal direction.

Once the first and second seal parts 690, 692 reach the spread (spread-out) position so that the sealing member 664 is in the closed position shown in FIG. 17B, the distal axle 696 is not able to move relative to the proximal axle 694. Between the position illustrated in FIG. 17A and the position illustrated in FIG. 17B, the distal axle 696 of the sealing member 664 moves a first axial distance relative to the proximal axle 694 of the sealing member 664.

When the calculus removing/retrieving device 650 reaches the position shown in FIG. 17B, further pulling on the plunger 668 causes the proximal axle 694 (lower axle part 694') to be released from the distal latch 699 so that the proximal axle 694 (lower axle part 694') can axially move in the rearward direction while being guided in the groove 695. Thus, the distal latch 699 is configured to retain or hold the proximal axle 694 until the distal axle 696 is positioned at the position shown in FIG. 17B and the sealing member 694 (two seal parts 690, 692) is in the spread position shown in FIG. 17B.

When the plunger 668 is further pulled in the rearward or proximal direction after the calculus removing/retrieving device 650 reaches the position shown in FIG. 17B, the sealing member 664 axially moves in the rearward or proximal direction within the tubular body 652. This rearward or proximal movement of the sealing member 664 results in calculus and fluid being drawn into the interior of the tubular body 652 by way of the inlet 654. At approximately the same time discharging of the fluid that has been introduced into the space between the proximal surface of the sealing member 694 and the closed end of the tubular body 652 by way of the outlet occurs, if the space between the proximal surface of the sealing member 694 and the closed end of the tubular body 652 has been filled by the fluid to some extent. With continued axial movement of the sealing member 664 in the tubular body 652, the sealing member eventually reaches the position illustrated in FIG. 17C in which the proximal axle 694 (lower axle part 694') is engaged by the proximal latch 698. The proximal axle 694 is thus held in this proximal-most axial position by the proximal latch 698 when the sealing member 664 is in the position shown in FIG. 17C.

Figure 17D:
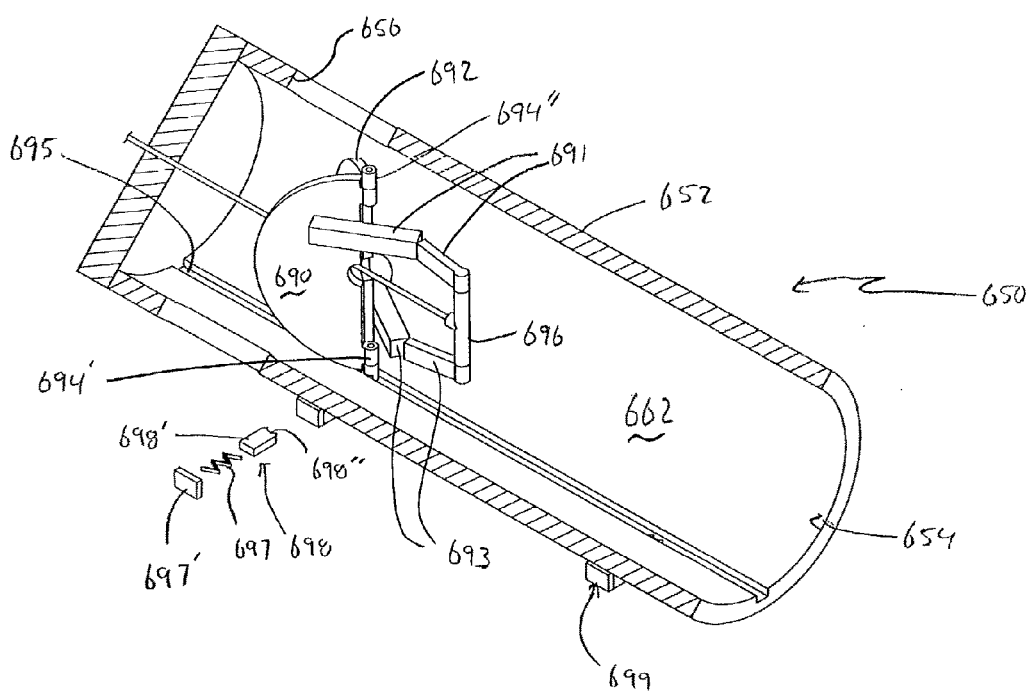
FIG. 17D is a perspective view of the calculus removing/retrieving device shown in FIG. 16 with the sealing member positioned at the proximal end of its movement stroke in the tubular body while the sealing member is in the folded or open position.

The plunger 668 is then moved in the forward or distal direction as generally illustrated in FIG. 17D. The proximal axle 694 is held by the proximal latch 698 during this initial forward movement of the plunger 668 and so the distal axle 696 moves relative to and away from the proximal axle 694 as generally shown in FIG. 17D. That is, the proximal axle 694 remains stationary, by virtue of being held by the proximal latch 698, while the distal axle 696 moves axially relative to the proximal axle 694 in a direction toward the inlet 654 of the tubular body 652. The movement of the distal axle 696 relative to the proximal axle 694 causes the first and second seal parts 690, 692 to shift from the spread position (closed sealing position) in which the sealing member 664 is closed to the folded position shown in FIG. 19D in which the sealing member 664 is open. In the open position of the sealing member 664, fluid is able to flow past the first and second seal parts 690, 692 so that when the plunger 668 is pushed and axially moved in the forward or distal direction, the plunger 668 and the sealing member 664 don't create both suction and exhaust, but rather only the position of the plunger 668 and the sealing member 664 changes. In addition, the barrier member covers enough (sufficient amount or area) of the inlet 654 to prevent retrieved calculus in the retrieval space 662 from being discharged through the inlet and expelled outside the device during the forward axial movement of the plunger 668 and the sealing member 664.

After the distal axle 696 has moved relative to the proximal axle 694 to the maximum extent permitted by the arms 691, 693 as shown in FIG. 17D, further pushing on the plunger 668 causes the proximal axle 694 to be released from the proximal latch 698. From the position illustrated in FIG. 17C to the position shown in FIG. 17D, the distal axle 696 moves a first axial distance which is the same as the first axial distance discussed earlier (i.e., the first axial distance moved by the distal axle between the FIG. 17A position and the FIG. 17B position.

After the proximal axle 694 is released by the proximal latch 698 due to continued pushing of the plunger 668, the sealing member 664 moves axially within the interior of the tubular body 652 while the first and second seal parts 690, 692 remain in the folded condition relative to one another (the folded condition shown in FIG. 17D) so that the sealing member 664 is in the open condition. Fluid which has been drawn or sucked into the interior of the tubular body 652 is able to flow past the sealing member. Calculus which has previously been retrieved and is located in the retrieval space 662 is not able to flow proximally past the folded seal parts 690, 692 of the sealing member 694 in the open position shown in FIG. 17D because the barrier member covers enough (sufficient amount or area) of the inlet 654 to prevent calculus from being discharged through the inlet 654. In addition, the calculus removing/retrieving device 650 can be equipped with a filter (similar to the filters 66, 166, 266, 366, 566 described above and illustrated in the drawing figures) that is specifically sized to permit the passage of fluid, yet prevent the passage of calculus in front of the sealing member 664. The calculus is thus retained in the space between the filter and the closed-state barrier member during the manipulation from FIG. 17A to 17D. With continued forward pushing of the plunger 668, the sealing member eventually reaches the distal end of the forward movement stroke of the plunger 668 and the proximal axle 694 (lower axle part 694') is engaged by the distal latch 699.

The operation described above is then repeated as many times as desired to draw additional calculus into the interior of the tubular body.

Figure 18A:
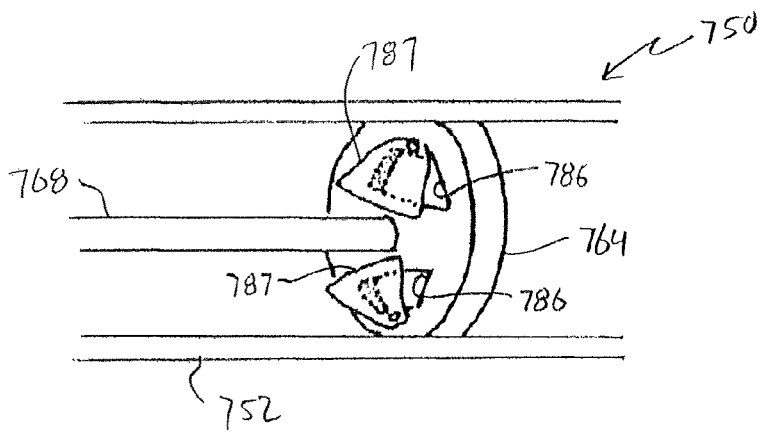
FIG. 18A is a perspective view of a portion of another embodiment of the calculus removing/retrieving device representing a further example of the calculus removing/retrieving device disclosed here.
Figure 18B:
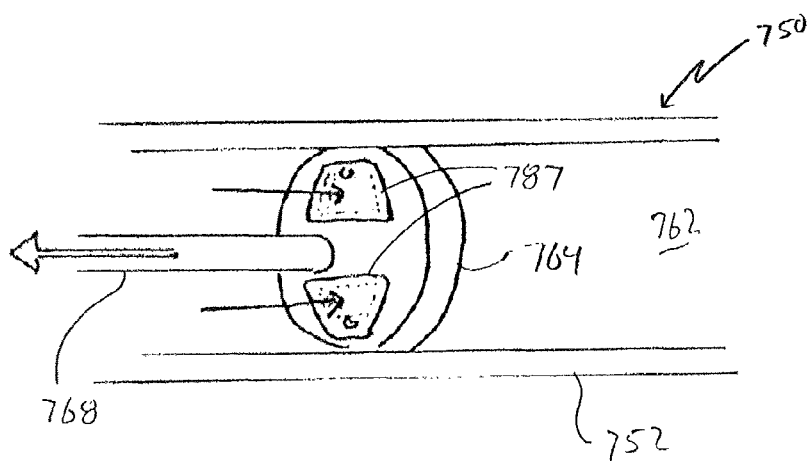
FIG. 18B is a perspective view of the portion of the calculus removing/retrieving device shown in FIG. 18A while the sealing member is moved in the rear or proximal direction.
Figure 18C:
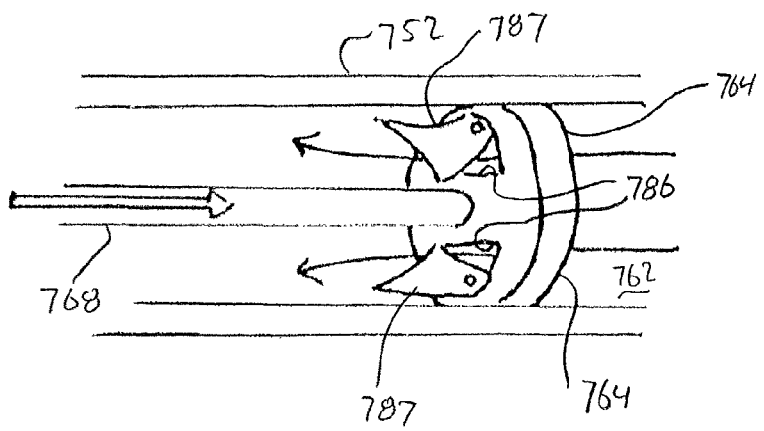
FIG. 18C is a perspective view of the portion of the calculus removing/retrieving device shown in FIG. 18A while the sealing member is moved in the forward or distal direction.

FIGS. 18A-18C illustrate a further embodiment of the device representing another example of the calculus removing/retrieving device and operational method disclosed here. Features of this embodiment which are similar to features described in the earlier embodiments are identified by common reference numerals, but preceded by a "7". A detailed description of features in this embodiment that are similar to features in earlier embodiments is not repeated, and the following detailed description focuses primarily on differences between this embodiment and the earlier embodiment.

FIGS. 18A-18C illustrate a portion of the calculus removing/retrieving device 750. This embodiment includes a plunger 768 connected to a sealing member 764. The sealing member 764 is disc-shaped and possesses an outer peripheral surface in substantial sealing contact with the inner surface of the elongated body (inner surface surrounding the lumen in the elongated body 752). The elongated body 752 can be configured in a manner similar to that shown in FIG. 2. The sealing member 764 includes a plurality of through holes 786 and a plurality of one way valves (flap valves or valve elements) 787 connected to the disc-shaped part of the sealing member 764. Each of the valves 787 is associated with a respective one of the through holes 786 so that valve 787 can move between an open position shown in FIG. 18C in which fluid flow through the through holes 786 is permitted and a closed position shown in FIG. 18B in which fluid flow through the through holes 786 is prevented. This embodiment of the calculus removing/retrieving device 750 can be used without the filter used in other embodiments. This embodiment preferably includes one of the barrier (cover members) used in other embodiments. The sealing member 764 together with the plunger 768 is positioned in the elongated member or tubular body 752, and is axially movable in the forward (distal) direction as well as the rearward (proximal) direction.

The operation of the calculus removing/retrieving device 750 is similar to operational aspects of other embodiments of the device described above. The calculus removing/retrieving device 750 can be connected to an operating member, for example the operating member 30 shown in FIG. 1. The calculus removing/retrieving device 750 is then inserted into the living body and advanced to the location of the calculus to be retrieved and removed. This can be accomplished in the manner described previously. When the inlet of the tubular body 752 is appropriately positioned for retrieval and removal of calculus (e.g., the inlet is positioned near the calculus to be retrieved and removed), the plunger 768 is axially moved in the rearward or proximal direction (by operating the operating member which pulls the manipulation wire and rearwardly moves the plunger 768). The rearward movement of the plunger 768 causes the sealing member 764 to also move in the rearward or proximal direction as illustrated in FIG. 18B. This rearward or proximal direction movement of the plunger and the sealing member 764 is identified by the left-most arrow in FIG. 18B. The other arrows in FIG. 18B depict the fluid flow (force) which urges the one-way valves 787 into covering relation to the respective through holes 786 so that the valves adopt a closed position. This rearward movement of the sealing member 764 draws calculus and fluid, located in the lumen of the living body, into the retrieval space 762 in the tubular body 752 through the inlet at the forward end (distal end) of the tubular body 752.

When the sealing member 764 reaches the end of its rearward stroke, the sealing member 764 is moved in the forward (distal) direction by pushing or moving the plunger 768 in the forward direction. This forward direction of movement of the plunger 768 and the sealing member 764 is identified by the left-most arrow in FIG. 18C. The other arrows in FIG. 18C depict the fluid flow (force) which urges the one-way valves 787 away from the respective through holes 786 so that the valves adopt an open position as shown in FIG. 18C. The valves 787 in the open position allow fluid to pass through the through holes 786 of the sealing member 764 as the sealing member 764 moves in the distal direction. Fluid in the retrieval space 362 is able to pass through the through holes 786 as indicated by the leftward-pointing arrows in FIG. 18C. The through holes 786 are sized or configured to permit fluid to pass through the through holes 786 while preventing calculus (calculi) from passing through the through holes 786. Each of the through holes 786 could be provided with a filter or screen covering the through hole 786 to help prevent calculus (calculi) from passing through the through holes 786.

When the sealing member 764 reaches the end of its forward stroke, the sealing member 764 is once again moved in the rearward direction by pulling or moving the plunger 768 in the rearward direction as discussed above. This rearward and forward movement of the sealing member 764 can be repeated to collect the desired amount of calculus in the retrieval space.

The detailed description above describes a device and method for retrieving/removing calculus from parts of a living body such as the ureter and the renal pelvis. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A device for retrieving calculus in a lumen of a living body comprising:
   an elongated member possessing an outer dimension configured to be positioned in the lumen of the living body, the elongated member including a lumen and possessing an inner surface surrounding the lumen, the elongated member also including an inlet, an outlet and a retrieval space in the lumen of the elongated member, the outlet being positioned proximally of the inlet and the retrieval space, and the retrieval space being located proximally of the inlet;
   a foldable sealing member movably positioned in the lumen of the elongated member to axially move in a distal direction in the lumen of the elongated member toward the inlet of the of the elongated member and to axially move in a proximal direction in the lumen of the elongated member;
   the foldable sealing member including at least one part that possesses an outer surface and is foldable so that the sealing member is shiftable between: an unfolded spread position in which the part is unfolded and spread out with the outer surface of the one part of the sealing member in sealing contact with the inner surface surrounding the lumen of the elongated member when a plunger is axially moved in the proximal direction to draw the calculus and fluid in the lumen of the living body into the retrieval space; and a folded position in which the one part is folded when the plunger is axially moved in the distal direction to permit fluid in the retrieval space to pass the foldable sealing member.

2. The device according to claim 1, wherein the foldable sealing member includes two parts that possess outer surfaces and are foldable relative to one another.

3. The device according to claim 2, wherein the sealing member includes a distal axle and a proximal axle that are spaced apart from one another, the proximal axle possessing a central axis and the distal axle possessing a central axis, the two parts being hingedly connected to the proximal axle so that the two parts rotate about the central axis of the proximal axle.

4. The device according to claim 2, wherein the two parts are foldable by virtue of the two parts being rotatably mounted to rotate about a common axis.

5. The device according to claim 2, wherein the sealing member includes a distal axle and a proximal axle that are spaced apart from one another, the proximal axle possessing a central axis and the distal axle possessing a central axis, further comprising a proximal latch fixedly mounted in the lumen of the elongated member and a distal latch fixedly mounted in the lumen of the elongated member, the proximal latch and the distal latch being spaced apart from each other, the proximal latch being positioned proximally of the distal latch, the proximal axle being held by the distal latch when the foldable sealing member is positioned at a distal-most position in the lumen of the elongated member.

6. The device according to claim 2, wherein the sealing member includes a distal axle and a proximal axle that are spaced apart from one another, the proximal axle possessing a central axis and the distal axle possessing a central axis, further comprising a proximal latch fixedly mounted in the lumen of the elongated member and a distal latch fixedly mounted in the lumen of the elongated member, the proximal latch and the distal latch being spaced apart from each other, the proximal latch being positioned proximally of the distal latch, the proximal axle being held by the proximal latch when the foldable sealing member is positioned at a proximal-most position in the lumen of the elongated member.

7. The device according to claim 2, wherein the sealing member includes a distal axle and a proximal axle that are spaced apart from one another, the distal axle and the proximal axle being connected via the two parts.

8. The device according to claim 7, wherein the elongated member is a tubular member that possesses a central axis, and wherein a central axis of the proximal axle and a central axis of the distal axle are both perpendicular to the central axis of the tubular member.

9. The device according to claim 2, wherein the sealing member includes a distal axle and a proximal axle that are spaced apart from one another, the proximal axle being connected to one of the two parts by a plurality of arms hinged to one another, the distal axle being connected to the other of the two parts by a plurality of arms hinged to one another.

10. A device for retrieving calculus in a lumen of a living body comprising:
an elongated member possessing a distal end portion and an outer dimension configured to permit the elongated member to be positioned in the lumen of the living body, the distal end portion of the elongated member being a tubular body possessing an interior surrounded by an inner surface;
the tubular body including an inlet, an outlet and a retrieval space in the interior at a position between the inlet and the outlet;
a foldable sealing member positioned in the interior of the tubular body and axially movable in a distal direction and in a proximal direction;
a plunger connected to the sealing member so that axial movement of the plunger axially moves the sealing member in the interior of the tubular body; and
the foldable sealing member being folded into a folded configuration when the plunger is axially moved in a distal direction toward the inlet and being spread out in a spread-out configuration when the plunger is axially moved in a proximal direction away from the inlet.

11. The device according to claim 10, wherein the foldable sealing member includes a distal axle and a proximal axle that are spaced apart from one another and movable relative to one another, each of the distal and proximal axles being positioned in the interior of the tubular body and possessing a respective central axis, and the foldable sealing member being folded about the central axis of the proximal axle.

12. The device according to claim 11, wherein the plunger possesses a distal end that is fixed to the distal axle.

13. The device according to claim 11, wherein the plunger possesses a distal end that is fixed to the distal axle so that axial movement of the plunger over a first axial distance axially moves the distal axle relative to the proximal axle while not moving the proximal axle and so that axial movement of the plunger over a second axial distance following the first axial distance moves the distal axle and the proximal axle together.

14. The device according to claim 10, wherein the foldable sealing member includes a distal axle and a proximal axle that are positioned in the interior of the tubular body and axially spaced apart from one another, and further comprising a distal latch and a proximal latch positioned in the interior of the tubular body in axially spaced apart relation to one another, the proximal axle engaging the distal latch during movement of the foldable sealing member in the distal direction, and the proximal axle engaging the proximal latch during movement of the foldable sealing member in the proximal direction.

15. The device according to claim 14, wherein the distal latch and the proximal latch are positionally fixed in the interior of the tubular body.

16. The device according to claim 10, wherein the foldable sealing member includes a distal axle and a proximal axle that are positioned in the interior of the tubular body and axially spaced apart from one another, and further comprising a distal latch and a proximal latch positioned in the interior of the tubular body in axially spaced apart relation to one another, the distal axle being axially movable in the distal direction relative to and away from the proximal axle during axial movement of the plunger in the distal direction over a first axial distance, the distal axle and the proximal axle being axially movable together in the distal direction during axial movement of the plunger in the distal direction over a second axial distance following the first axial distance, during axial movement of the plunger in the distal direction over the first axial distance the proximal latch engages the proximal axle to positionally fix the proximal axle while the distal axle axially moves in the distal direction relative to and away the proximal axle, and during axial movement of the plunger in the distal direction over the second axial distance the proximal axle and the distal axle axially move together until the proximal axle is engaged by the distal latch.

17. The device according to claim 10, wherein the foldable sealing member includes a distal axle and a proximal axle that are positioned in the interior of the tubular body and axially spaced apart from one another, and further comprising a distal latch and a proximal latch positioned in the interior of the tubular body in axially spaced apart relation to one another, the distal axle being axially movable in the proximal direction relative to the proximal axle during axial movement of the plunger in the proximal direction over a first axial distance, the distal axle and the proximal axle being axially movable together in the proximal direction during axial movement of the plunger in the proximal direction over a second axial distance following the first axial distance, during axial movement of the plunger in the proximal direction over the first axial distance the distal latch engages the proximal axle to positionally fix the proximal axle while the distal axle axially moves in the proximal direction relative to and toward the proximal axle, and during axial movement of the plunger in the proximal direction over the second axial distance the proximal axle and the distal axle axially move together until the proximal axle is engaged by the proximal latch.

18. The device according to claim 10, wherein the foldable sealing member includes two parts that are foldable relative to one another, the foldable sealing member also including a distal axle and a proximal axle, the proximal axle being connected to one of the two parts by a plurality of arms hinged to one another, the distal axle being connected to the other of the two parts by a plurality of arms hinged to one another.

19. The device according to claim 10, wherein the sealing member includes a filter configured to allow the fluid in the retrieval space to pass through the filter while preventing the calculus in the retrieval space from passing through the filter.

20. The device according to claim 10, further comprising a barrier positioned at the inlet to the elongated member, the barrier including at least one cover part movable between an open position permitting the calculus to be drawn through the inlet and into the retrieval space when the sealing member is moved in the proximal direction and a closed position in which the cover part covers a part of the inlet to prevent the calculus located in the retrieval space from flowing out through the inlet when the sealing member is moved in the distal direction.

* * * * *